(12) United States Patent
Bosch et al.

(10) Patent No.: US 7,902,102 B2
(45) Date of Patent: Mar. 8, 2011

(54) PENTASIL-STRUCTUER ZEOLITHIC MATERIAL THE PRODUCTION AND USE THEREOF

(75) Inventors: Marco Bosch, Mannheim (DE); Ulrich Müller, Neustadt (DE); Matthias Frauenkron, Freinsheim (DE)

(73) Assignee: BASF SE, Ludwigshafen (DE)

( * ) Notice: Subject to any disclaimer, the term of this patent is extended or adjusted under 35 U.S.C. 154(b) by 1193 days.

(21) Appl. No.: 10/581,311

(22) PCT Filed: Dec. 2, 2004

(86) PCT No.: PCT/EP2004/013733
§ 371 (c)(1),
(2), (4) Date: Jun. 2, 2006

(87) PCT Pub. No.: WO2005/053842
PCT Pub. Date: Jun. 16, 2005

(65) Prior Publication Data
US 2007/0135637 A1    Jun. 14, 2007

(30) Foreign Application Priority Data

Dec. 2, 2003 (DE) ................. 103 56 184

(51) Int. Cl.
*B01J 29/06* (2006.01)
*C01B 39/02* (2006.01)
(52) U.S. Cl. .......... 502/60; 502/63; 502/64; 502/68; 502/71; 502/77; 423/700; 423/702; 423/704; 423/707
(58) Field of Classification Search .......... 502/60, 502/63, 64, 68, 71, 77; 423/700, 702, 704, 423/707
See application file for complete search history.

(56) References Cited

U.S. PATENT DOCUMENTS

| | | | |
|---|---|---|---|
| 3,702,886 A | 11/1972 | Argauer et al. |
| 3,709,979 A | 1/1973 | Chu |
| 5,053,374 A | 10/1991 | Absil et al. |
| 5,614,079 A | 3/1997 | Farnos et al. |
| 5,731,449 A | 3/1998 | Li et al. |
| 5,741,906 A | 4/1998 | Santiesteban et al. |
| 6,077,984 A | 6/2000 | Drake et al. |
| 6,084,096 A | 7/2000 | Li et al. |
| 6,380,119 B1 | 4/2002 | Grosch et al. |
| 6,458,187 B1 | 10/2002 | Fritz et al. |
| 6,555,688 B1 | 4/2003 | Klockemann et al. |
| 6,562,971 B2 | 5/2003 | Frauenkron et al. |
| 6,627,756 B1 | 9/2003 | Riechers et al. |
| 6,710,002 B2 | 3/2004 | Grosch et al. |
| 6,958,397 B2 | 10/2005 | Frauenkron et al. |
| 6,967,181 B2 | 11/2005 | Muller et al. |
| 2002/0072467 A1 | 6/2002 | Ogawa |
| 2002/0082159 A1 | 6/2002 | Grosch et al. |
| 2002/0107394 A1 | 8/2002 | Frauenkron et al. |
| 2003/0139598 A1 | 7/2003 | Frauenkron et al. |
| 2004/0014591 A1 | 1/2004 | Muller et al. |
| 2004/0152583 A1 | 8/2004 | Grosch et al. |
| 2004/0236106 A1 | 11/2004 | Frauenkron et al. |
| 2006/0046929 A1 | 3/2006 | Hofstadt et al. |
| 2006/0116517 A1 | 6/2006 | Bosch et al. |

FOREIGN PATENT DOCUMENTS

| | | |
|---|---|---|
| CN | 1240193 A | 1/2000 |
| CN | 1371377 A | 9/2002 |
| DE | 197 23 949 A1 | 12/1998 |
| DE | 19826209 | 12/1999 |
| DE | 199 33 850 A1 | 1/2001 |
| DE | 10219879 | 11/2003 |
| DE | 102 32 406 A1 | 1/2004 |
| DE | 10326137 | 12/2004 |
| DE | 10356184 | 7/2005 |
| EP | 0130407 | 1/1985 |
| EP | 0349859 | 1/1990 |
| EP | 0382055 | 8/1990 |
| EP | 0712662 | 5/1996 |
| EP | 831096 | 3/1998 |
| EP | 0831096 | 3/1998 |
| EP | 0842936 | 5/1998 |
| EP | 0952152 | 10/1999 |
| EP | 1053786 | 11/2000 |
| EP | 1192993 | 4/2002 |
| EP | 1 215 211 A1 | 6/2002 |
| JP | 3132061 | 6/1991 |
| JP | 5017460 | 1/1993 |
| JP | 5017461 | 1/1993 |
| JP | 5017462 | 1/1993 |
| WO | WO-91/04943 | 4/1991 |
| WO | WO-97/03019 | 1/1997 |
| WO | WO-98/55228 | 12/1998 |
| WO | WO-01/02404 A2 | 1/2001 |
| WO | WO-01/02404 A3 | 1/2001 |

(Continued)

OTHER PUBLICATIONS

G.T. Kokotailo et al, 1978. "Synthesis and structure of synthetic zeolite ZSM-11," *Nature* vol. 275 Sep. 14, 1978; pp. 119-120.
Kokotailo et al., 1978. "Structure of synthetic zeolite ZSM-5" *Nature* vol. 272, Mar. 30 pp. 437-438.
Jacobs et al., 1987. "Chapter I: Synthesis of ZSM-5 Zeolites in the Presence of Tetrapropylammonium Ions" *Synthesis of High-Silica Aluminosilicate Zeolites, Studies in Surface Science and Catalysis* vol. 33, Elsevier, Amsterdam 1987, 47-111.
Cundy et al, 1993. "Crystallisation of Zeolitic Molecular Sieves: Direct Measurements of the Growth Behaviour of Single Crystals as a Function of Synthesis Conditions." *Faraday Discuss* 95, pp. 235-252.
A.E. Persson et al, 1995. "Synthesis of stable suspensions of discrete colloidal zeolite (Na, TPA) ZSM-5 crystals" *Zeolites* 15:611-619.

(Continued)

*Primary Examiner* — Elizabeth D Wood
(74) *Attorney, Agent, or Firm* — Connolly Bove Lodge & Hutz LLP

(57) ABSTRACT

Zeolite material of the pentasil type has an alkali metal and alkaline earth metal content of not more than 100 ppm and a molar ratio of Si to Al of from 250 to 1500, at least 90% of the primary particles of the zeolite material being spherical and 95% by weight of the spherical primary particles having a diameter of less than or equal to 1 μm.

13 Claims, 6 Drawing Sheets

FOREIGN PATENT DOCUMENTS

Figure 1:
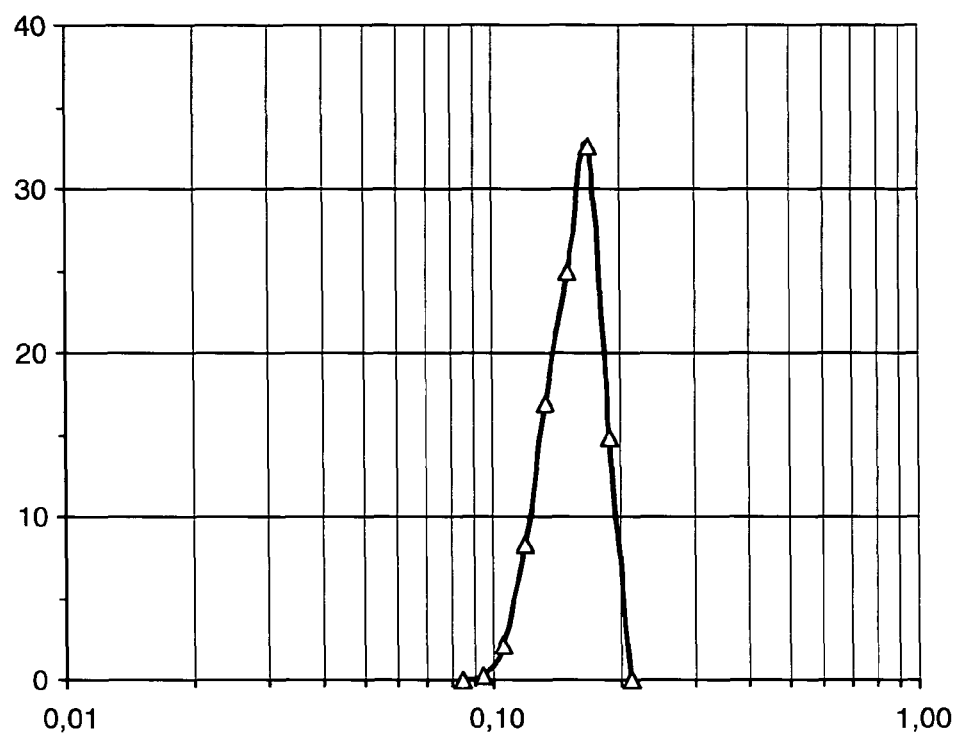

| | | |
|---|---|---|
| WO | WO-0123089 | 4/2001 |
| WO | WO-02086946 | 10/2002 |
| WO | WO-03/004499 A1 | 1/2003 |
| WO | WO-2005053842 | 6/2005 |

OTHER PUBLICATIONS

Reding et al, 2003. "Comparing synthesis routes to nano-crystalline zeolite ZSM-5" Microporous and Mesoporous Materials, vol. 57, No. 1,2, January 83-92.

Mostowicz et al., 1995. "Factors Influencing the Crystal Morphology of ZSM-5 Type Zeolites" Zeolites, pp. 65-72.

Ch Baelocher et al., 2001. *Atlas of Zeolite Structure Types*, Elsevier, 5th Edition, Amsterdam 2001, pp. 184-185.

Perego et al, 1984. "Ordered and Disordered Structures in Borosilicates with a Pentasil-Type Framework." *J. Appl. Cryst.* vol. 17, pp. 403-410.

R. Van Grieken et al., 2000. "Anomalous crystalllization mechanism in the synthesis of nanocrystalline ZSM-5" *Microporous and Mesoporous Materials* vol. 39, pp. 135-147.

"Catalog of Disorder in Zeolite Frameworks" http://www.iza-structure.org/databases/ H. Gies and H. van Koningsveld. Published on behalf of the Structure Commission of the International Zeolite Association.

W.T. Reichle, "Reactions of Aliphatic $\alpha$-$\omega$-Diamines in H+-Pentasils", Journal of Catalysis 144, pp. 556-568 (1993).

Huber, G. et al., "Hydrothermal Stability of Co/SiO2 Fischer-Tropsch Synthesis Catalysts" Studies in Surface Science and Catalysis, Elsevier, 139 (2001), p. 423-430.

Ullman's Encyclopedia of Industrial Chemistry, 6th Edition, 2000 Electronic Release, Chapter 3.2.

Ullmann's Encyclopedia of Industrial Chemistry, 6th Edition, 2000 Electronic Release, Chapter 6.3.2.

Ullmann's Encyclopedia of Industrial Chemistry, 6th Edition, 2000 Electronic Release, Chapter 7.6.

Ullmann's Encyclopedia of Industrial Chemistry, 6th Edition, 2000 Electronic Release, Chapter 8.3.2.

Weitkamp, J. et al. (Editors), Catalysis and Zeolites, Fundamentals and Applications, Springer Verlag, Chapter 3.3.3.3, pp. 142-144.

Tanabe, K. et al., "New Solid Acids and Bases, Their Catalytic Properties", Studies in Surface Science and Catalysis, Elsevier, 51 (1989), p. 152.

PENTASIL-STRUCTUER ZEOLITHIC MATERIAL THE PRODUCTION AND USE THEREOF

This application is a National Phase filing of PCT/EP2004/013733, filed Dec. 2, 2004, claiming priority to German application DE 103 56 184.6, filed Dec. 2, 2003.

The present invention relates to a zeolite material of the pentasil structure type, in particular of the structure type ZSM-5, having an alkali metal and alkaline earth metal content of not more than 150 ppm and a molar ratio of Si to Al in the range of from 250 to 1500, wherein at least 95% by weight of the spherical primary particles of the zeolite material have a diameter in the range of less than or equal to 1 µm and at least 90% preferably at least 95% of all primary particles are spherical. The present invention also relates to a molding which contains this zeolite material and the use of the zeolite material as such or of the molding as a catalyst. The present invention furthermore relates to a special process in which the zeolite material or the molding which contains this material is used as a catalyst.

In all industrial chemical processes in which catalysts are used, attempts are made to increase the life of the catalysts and hence the time for which it is possible to operate without changing the catalyst and hence without intervention in the process. One measure in this context is to reduce the particle size of the catalysts. In the case of a crystalline catalyst material, for example a zeolite catalyst, this means that the size of the crystals, in particular of the zeolite crystals, should be kept as small as possible.

Zeolites are known to be crystalline aluminosilicates having ordered channel and cage structures which have micropores which are preferably smaller than about 0.9 nm. The network of such zeolites is composed of $SiO_4$ and $AlO_4$ tetrahedra which are linked via common oxygen bridges. An overview of the known structures is to be found, for example, in W. M. Meier, D. H. Olson and Ch. Baerlocher, "Atlas of Zeolite Structure Types", Elsevier, 5th Edition, Amsterdam 2001. In detail particularly the types assigned by X-ray analysis to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI, EMT, EPI, ERI, ESV, EUO, FAU, FER, GIS, GME, GOO, HEU, IFR, ISV, ITE, JBW, KFI, LAU, LEV, LIO, LOS, LOV, LTA, LTL, LTN, MAZ, MEI, MEL, MEP, MER, MFI, MFS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG and ZON structure and to mixed structures of two or more of the abovementioned structures are to be mentioned.

Depending on the field of use of the catalyst, the catalyst must have, besides the crystal size, a certain pore size or pore distribution. For example, in the preparation of triethylenediamine, the use of a zeolite catalyst of the structure type ZSM-5 has proven useful. In addition to the properties described above, the catalyst must also have a certain chemical composition. In the case of the ZSM-5 catalyst, for example, a certain molar ratio of Si to Al in the zeolite material is advantageous.

The use of a zeolite catalyst of the structure type ZSM-5 in the preparation of triethylenediamine is described, for example, in WO 01/02404, the molar ratio of Si to Al being from 100 to 700, particularly preferably from 150 to 250. No information is given concerning the exact preparation of the zeolite active material.

WO 03/004499 describes a process for the selective synthesis of triethylenediamine using a zeolite catalyst, in particular a zeolite catalyst of the ZSM-5 type, which has a molar ratio of Si to a metal M in the range of greater than 100, preferably greater than 200, more preferably from greater than 300 to 40 000, particularly preferably from 400 to 5000. The metal M, which may occur in the oxidation state III or IV, is selected from the group of Al, B, Fe, Co, Ni, V, Mo, Mn, As, Sb, Bi, La, Ga, In, Y, Sc, Cr and mixtures thereof and Ti, Zr, Ge, Hf, Sn and mixtures thereof, respectively. Aluminosilicate is particularly preferred here. In the example according to the present invention, a sodium aluminosilicate having a ratio of Si to Al of 1000 is used. Nothing is said about particle sizes in this document.

EP 1 215 211 A1 describes a process for the preparation of triethylenediamine, in which the catalyst used is a zeolite catalyst which contains one or more metals M in the oxidation states II, III or IV as oxides, and, where in the case of M being Al, the molar ratio of $SiO_2$ to $Al_2O_3$ is greater than 1400. In addition to ZSM-5, further catalysts of the structure type ZSM-11, ZSM-23, ZSM-53, NU-87, ZSM-35 and mixed structures are disclosed. Nothing is said about the crystal size of the zeolite material in this publication, and the only example relates to a zeolite material which contains Si and Ti and hence no Al.

The preparation of a zeolite material of the ZSM-5 type is described in R. Mostowicz and J. M. Berak, Zeolites (1985), 65-72. The crystals disclosed there have sizes of substantially greater than 1 µm. Furthermore, this publication states that the ratio of Si to Al has no influence on the crystal size. Ratios of Si to Al of 30 and 90 are explicitly described.

G. Reding, T. Mäurer and B. Kraushaar-Czarnetzki, Microporous and Mesoporous Materials 57 (2003), 83-92 describe the preparation of a nanocrystalline ZSM-5 material comprising crystals having a diameter of less than or equal to 100 nm. However, the molar ratio Si to Al is 60. In contrast to the abovementioned publication, Reding et al. state that, depending on the preparation process, the presence of aluminum has a considerable influence on the particle size distribution.

A. E. Persson, B. J. Schoemann, J. Sterte and J.-E. Otterstedt, Zeolites 15 (1995), 611-619 describe the preparation of a ZSM-5 material having particle sizes in the range of from 130 to 230 nm. However, the molar ratio of Si to Al is in the range of from about 50 to about 230. In order to obtain small particles, this publication expressly recommends synthesizing ZSM-5 with a low ratio of $SiO_2$ to $Al_2O_3$. In contrast to a literature reference cited in this publication (C. S. Cundy, B. M. Lowe, D. M. Sinclair, Faraday Discuss. 95 (1993), 235-252), according to which the particle size increases with increasing aluminum concentration, Persson et al. found the opposite effect. According to Persson et al., the zeolite material was prepared using NaOH and also NaCl. Experiments without the addition of a sodium compound led to a decreasing crystal formation rate.

P. A. Jacobs, J. A. Martens, Synthesis of High-Silica Aluminosilicate Zeolites, Studies in Surface Science and Catalysis, Volume 33, Elsevier, Amsterdam 1987, describe, on page 74 of this literature reference, inter alia that, in the preparation of ZSM-5, the simultaneous changing of two parameters (for example the molar ratio of Si to Al, the salt addition, the $SiO_2$ source, the alkalinity of the synthesis system) gives unexpected results which are difficult to predict. For example, crystal structures at a high molar ratio of Si to Al of 750, which have the appearance of intergrown disks, are described. Accordingly, P. A. Jacobs et al. describe substantially lower Si to Al ratios which are of the order of magnitude of from 14 to 45.

In view of this prior art, it is an object of the present invention, inter alia, to provide a zeolite material which has a high molar ratio Si to Al and simultaneously has very small crystals and moreover an extremely low alkali metal and alkaline earth metal content.

Accordingly the present invention relates to a zeolite material of the pentasil structure type having an alkali metal and alkaline earth metal content of not more than 150 ppm and a molar ratio of Si to Al of from 250 to 1500, wherein at least 90% of the primary particles of the zeolite material are spherical and at least 95% by weight of the spherical primary particles have a diameter of less than or equal to 1 μm.

Concerning the term "pentasil structure type" as used in the context of the present patent application, reference is made to the abovementioned literature W. M. Meier, D. H. Olson and Ch. Baerlocher, Atlas of Zeolite Structure Types, Elsevier, 5th Edition, Amsterdam 2001. Examples for zeolites with the pentasil structure type are for example zeolites with MFI-structure, with MEL-structure or with mixed MFI-MEL-structure. Further information concerning the pentasil structure can be found for example posted in the internet by the International Zeolite Association using the following address: "http://topaz.ethz.ch/IZA-SC/DisordStructures.htm" as well as in the literature cited on this page in the category "Pentasils": G. T. Kokotailo et. al., Nature 272 (1978) 437; G. T. Kokotailo et. al., Nature 275 (1978) 119; G. Perego, M. Cesari, J. Appl. Cryst 17 (1984) 403.

The term "structure type ZSM-5" as used in the context of the present invention denotes a zeolite material as described in W. M. Meier, D. H. Olson and Ch. Baerlocher, Atlas of Zeolite Structure Types, Elsevier, 5th Edition, Amsterdam 2001, pages 184-185, as a zeolite of the structure type ZSM-5.

According to a preferred embodiment of the present invention, at least 96, more preferably at least 97, more preferably at least 98, in particular at least 99, % by weight of the spherical primary particles of the zeolite material have a diameter of less than or equal to 1 μm.

The term "spherical" as used in the context of the present invention denotes primary particles which, on investigation by scanning electron microscopy (SEM) at a magnification of from $0.5 \cdot 10^4$ to $2.0 \cdot 10^4$, are substantially free of sharp edges. Accordingly, the term "spherical" denotes, for example, purely spherical or deformed spherical, for example elliptical or cuboid primary particles, wherein the edges are rounded and not sharp in the case of the cuboid primary particles in the abovementioned investigation method in said resolution range.

According to a more preferred embodiment of the present invention, at least 91, more preferably at least 92, more preferably at least 93, more preferably at least 94, more preferably at least 95, more preferably at least 96, in particular at least 97, % of the primary particles of the zeolite material are spherical.

The term alkali metal and alkaline earth metal content as used in the context of the present invention denotes the content of alkali metal, calculated as alkali metal oxide, and alkaline earth metal, calculated as alkaline earth metal oxide, in the zeolite material, whereas the term alkali metal is to be understood as meaning the sum of all alkali metals and the term alkaline earth metal is to be understood as meaning the sum of all alkaline earth metals, calculated in each case as the corresponding oxides.

According to a preferred embodiment of the present invention, the alkali metal and alkaline earth metal content of the zeolite material is not more than 125 ppm, more preferably not more than 100 ppm, more preferably not more than 75 ppm, particularly preferably not more than 50 ppm. In the context of the present invention, alkali metal and alkaline earth metal contents of the zeolite material of not more than 25 ppm and/or not more than 10 ppm are also possible.

Accordingly, the present invention also relates to a zeolite material as described above, wherein the alkali metal and alkaline earth metal content is not more than 100 ppm.

The alkali metal and alkaline earth metal content of the zeolite material was determined for the purposes of the present invention according to the method described below: from 0.1 to 0.4 g of a sample of the zeolite material was weighed into a platinum dish and 10 ml each of sulfuric acid and hydrofluoric acid were added. Thereafter, heating was effected on a hotplate and evaporation to dryness was carried out. After cooling, concentrated hydrochloric acid and about the same volume of water were added to the residue and the latter was dissolved with heating. The solution obtained was washed quantitatively into a 50 ml volumetric flask and made up to the mark with water. As a rule, a blank patch was prepared in a corresponding manner. The solutions thus prepared were analyzed by atomic absorption using the flame technique for the elements to be determined. In the atomic absorption spectrometer, the combustion gas used was $C_2H_2$/air.

Regarding the primary particles of the zeolite material, diameters of less than 1 μm are preferred. More preferred are diameters of not more than 900 nm, more preferably not more than 800 nm, more preferably not more than 700 nm, more preferably not more than 600 nm, particularly preferably not more than 500 nm. More preferably, the primary particles of the zeolite material have a diameter in the range of at least 10 nm, more preferably at least 20 nm, more preferably at least 30 nm, more preferably at least 40 nm, particularly preferably at least 50 nm. The diameters are particularly preferably in the range of from 50 to 500 nm, more particularly preferably in the range of from 50 to 400 nm, more particularly preferably in the range of from 50 to 300 nm, more particularly preferably in the range of from 50 to 250 nm, very particularly preferably in the range of from 50 to 200 nm.

The present invention accordingly also relates to a zeolite material as described above, wherein the diameters of the primary particles of the zeolite material are in the range of from 50 to 250 nm.

According to a further embodiment of the present invention, the diameter may also be in the range of from 50 to 100 nm or in the range of from 100 to 150 nm or in the range of from 150 to 200 nm or in the range of from 200 to 250 nm.

The diameters of the primary particles as described in the context of the present invention may be determined, for example, via the electron microscopic methods SEM (scanning electron microscopy) and TEM (transmission electron microscopy). The diameters described in the context of the present invention were determined by SEM.

Regarding the molar ratio of Si to Al in the zeolite material, this is preferably in the range of from 300 to 1000, more preferably in the range of from 300 to 900, more preferably in the range of from 300 to 800, more preferably in the range of from 300 to 700, particularly preferably in the range of from 350 to 600.

Accordingly, the present invention also relates to a zeolite material as described above, wherein the molar ratio of Si to Al is in the range of from 350 to 600.

According to further embodiments of the present invention, the molar ratios of Si to Al may also be in the range of from 400 to 600 or from 450 to 500.

The crystalline zeolite material of the pentasile structure type according to the present invention, in particular of the structure type ZSM-5, preferably has a monodisperse particle distribution, wherein the coefficient of variation is less than 50%, preferably less than 25%, even more preferably less than 10%. In this context the coefficient of variation indicates, percentage of the standard deviation from the arithmetic average. The coefficient of variation is thus equal to 100*(delta (X)/X), wherein delta(X) represents the standard deviation and X the arithmetic average of the particle size distribution. The particle size distribution is done in this context using laser diffraction spectrometry according to DIN 13320.

The specific surface area of the crystalline zeolite material according to the present invention, determined according to DIN 66131 (BET), is in general at least 350, preferably at least 400, particularly preferably at least 425, m$^2$/g. For example, the specific surface area is preferably from 350 to 500, more preferably from 400 to 500, particularly preferably from 425 to 500, m$^2$/g.

The pore volume of the crystalline zeolite material according to the present invention, determined according to DIN 66134 (Langmuir), is in general at least 0.6, preferably at least 0.7, particularly preferably at least 0.8, ml/g. For example, the pore volume is preferably from 0.6 to 1.5, more preferably from 0.7 to 1.4, particularly preferably from 0.8 to 1.3, ml/g.

The zeolite material according to the present invention, can generally be prepared according to all suitable processes which lead to the zeolite material of the pentasil structure type as specified above and particularly preferably to the ZSM-5 structure type. Regarding possible pentasil structure types, reference may be made to the above list. As examples the structure types MFI, MEL and the mixed structure of MFI and MEL are mentioned.

In general, said zeolites of the pentasil structure type, in particular of the structure type ZSM-5, are prepared by reacting a mixture of an SiO$_2$ source and of an Al source and a nitrogen-containing base as a template, optionally also with addition of at least one basic compound, under autogenous pressure or under superatmospheric pressure in a pressure-resistant container at elevated temperatures in a period of from several hours to a few days, wherein a crystalline product is formed. Said crystalline product is isolated, washed, dried, and calcined at elevated temperatures to remove the organic nitrogen base. In the powder thus obtained, aluminum is at least partly present within the zeolite lattice in alternating proportions with 4-, 5- or 6-fold coordination.

The process according to the present invention is distinguished, inter alia, by the fact that, in contrast to many processes which are described in the prior art, no sodium compound and also no other alkali metal compound and/or alkaline earth metal compound are used as initiators. This avoids the situation where alkali metal and/or alkaline earth metal have to be removed, in at least one additional reaction step, from the zeolite material, which should contain only very small amounts, described above, of alkali metal, or from one of its intermediates.

Accordingly, the present invention also describes a process as described above, wherein no alkali metal compound and no alkaline earth metal compound are used as initiating material and/or starting material in the synthesis of the at least one zeolite material.

According to a preferred embodiment, the present invention therefore relates to a process for the preparation of a zeolite material as described above, comprising the steps (i) preparation of a mixture containing at least one SiO$_2$ source, at least one aluminum source and at least one template compound, wherein the mixture contains not more than 150 ppm of alkali metal and alkaline earth metal and wherein the at least one SiO$_2$ source and the at least one aluminum source are used in a ratio which permits the formation of a crystalline material having a molar ratio of Si to Al in the range of from 250 to 1500;

(ii) reaction of the compounds contained in the mixture to give a mother liquor containing crystalline material, said crystalline material containing at least a portion of at least one template compound;

(iii) separation of the crystalline material from the mother liquor;

(iv) removal of the at least one template compound from the crystalline material.

The term "primary particle" as used in the context of the present invention denotes particles which are formed exclusively by covalent interaction and in which no Van der Waals interactions are involved in the composition of an individual particle. In the context of the present invention, the term "primary particle" relates to crystals which result from the separation from the mother liquor according to step (iii) described above.

As SiO$_2$ sources all compounds which permit the preparation of the zeolite material according to the present invention may be used. Preferably, silicic acid or a silica sol or a mixture of two or more different silica sols or a tetraalkoxysilane or a mixture of two or more different tetraalkoxysilanes or a mixture of at least one silica sol and at least one tetraalkoxysilane or a mixture of silicic acid and at least one silica sol or a mixture of silicic acid and at least one silica sol and at least one tetraalkoxysilane is preferably used.

Very generally, in the context of the present invention, compounds or mixtures of compounds of the composition $$Si(OR)_{4-x}(OR')_x$$

where x is 0, 1, 2, 3 or 4, may be used as SiO$_2$ source, where R and R' may be different from one another and may each be hydrogen, C$_1$-C$_8$-alkyl, for example methyl, ethyl, n-propyl, isopropyl, n-butyl, isobutyl, tert-butyl, pentyl, hexyl, heptyl or octyl, C$_4$-C$_8$-cycloalkyl, such as cyclobutyl, cyclopentyl, cyclohexyl, cycloheptyl or cyclooctyl, aryl, alkylaryl or arylalkyl, or where R and R' may be identical and may each be hydrogen, C$_1$-C$_8$-alkyl, for example methyl, ethyl, n-propyl, isopropyl, n-butyl, isobutyl, tert-butyl, pentyl, hexyl, heptyl or octyl, C$_4$-C$_8$-cycloalkyl, such as cyclobutyl, cyclopentyl, cyclohexyl, cycloheptyl or cyclooctyl, aryl, alkylaryl or arylalkyl.

According to a preferred embodiment of the process according to the present invention, the SiO$_2$ source used is a compound of the general composition $$Si(OR)_4$$

or of the general composition $$Si(OR)_3(OR')$$

where R' is hydrogen and R is C$_1$-C$_8$-alkyl, for example methyl, ethyl, n-propyl, isopropyl, n-butyl, isobutyl, tert-butyl, pentyl, hexyl, heptyl or octyl.

Very particularly preferably, a compound of the general composition $$Si(OR)_4$$

is employed as SiO$_2$ source.

where R is C$_1$-C$_8$-alkyl, for example methyl, ethyl, n-propyl, isopropyl, n-butyl, isobutyl, tert-butyl, pentyl, hexyl, heptyl or octyl, more preferably methyl, ethyl, n-propyl, isopropyl, n-butyl, isobutyl or tert-butyl, more preferably methyl, ethyl, n-propyl or isopropyl, more preferably methyl or ethyl, particularly preferably ethyl.

All compounds which permit the preparation of the zeolite material according to the present invention may be used as the aluminum source. In the process according to the present invention, the use of aluminum nitrate, aluminum sulfate or a trialkoxyaluminate of the composition $Al(OR)_3$ or a mixture of two or more of these compounds as aluminum source is particularly preferred. Regarding the trialkoxyaluminates of the composition $Al(OR)_3$, the radicals R may be identical or different from one another and are $C_1$-$C_8$-alkyl, for example methyl, ethyl, n-propyl, isopropyl, n-butyl, isobutyl, tert-butyl, pentyl, hexyl, heptyl or octyl, $C_4$-$C_8$-cycloalkyl, such as cyclobutyl, cyclopentyl, cyclohexyl, cycloheptyl or cyclooctyl, aryl, alkylaryl or arylalkyl.

According to a very particularly preferred embodiment of the process according to the present invention, the aluminum source used is aluminum sulfate octadecahydrate.

All compounds which permit the preparation of the zeolite material according to the present invention may be used as template compound. In the process according to the present invention, tetraalkylammonium hydroxides of the composition

[NRR'R''R''']$^+$OH$^-$ where R, R', R'' and R''' may be identical or different from one another and may each be hydrogen, $C_1$-$C_8$-alkyl, for example methyl, ethyl, n-propyl, isopropyl, n-butyl, isobutyl, tert-butyl, pentyl, hexyl, heptyl or octyl, $C_4$-$C_8$-cycloalkyl, such as cyclobutyl, cyclopentyl, cyclohexyl, cycloheptyl or cyclooctyl, are particularly preferably used as the template compound. According to a further preferred embodiment of the process according to the present invention, R, R', R'' and R''' are more preferably $C_1$-$C_8$-alkyl, for example methyl, ethyl, n-propyl, isopropyl, n-butyl, isobutyl, tert-butyl, pentyl, hexyl, heptyl or octyl, more preferably n-propyl or isopropyl, particularly preferably n-propyl.

Accordingly, the present invention also relates to a process as described above, wherein a tetraalkoxysilane is used as $SiO_2$ source, an aluminum sulfate as the aluminum source and tetraalkylammonium hydroxide as template compound.

According to a particularly preferred embodiment, the mixture according to (i) additionally contains water.

According to a particularly preferred embodiment, tetraethoxysilane is used as the $SiO_2$ source, aluminum sulfate octadecahydrate as aluminum source and tetrapropylammonium hydroxide as template compound in the process according to the present invention.

Accordingly, the present invention also describes a process as described above, wherein, according to (i), a mixture containing tetraethoxysilane, aluminum sulfate octadecahydrate, tetrapropylammonium hydroxide and water is prepared.

The abovementioned compounds contained in the mixture according to (i) are used in molar ratios which permit the preparation of the zeolite material according to the present invention, in particular with the molar ratios of Si to Al, described above, in the range of from 250 to 1500. A synthesis gel which has the following molar composition is preferably used as the mixture according to (i), wherein Si in the at least one $SiO_2$ source is calculated as $SiO_2$, Al in the at least one aluminum source is calculated as $Al_2O_3$ and the abbreviation TMP refers to the template compound

xTMP.$SiO_2$.y$Al_2O_3$.z$H_2O$ and wherein x=0.2 to 1.0, y=2.5·$10^{-4}$ to 25·$10^{-4}$ and z=15 to 100.

In general, the synthesis gel, the mixture according to (i), has an alkali metal and alkaline earth metal content of not more than 100 ppm, preferably not more than 50 ppm, more preferably not more than 25 ppm, particularly preferably not more than 10 ppm.

The order of addition of the components of the synthesis gel is as a rule not critical. According to a preferred embodiment of the process according to the present invention, a solution or suspension or preferably a solution of the at least one template compound, is initially taken, and the at least one $SiO_2$ source is added to this solution. This addition preferably takes place at from 5 to 40° C., more preferably from 15 to 35° C., particularly preferably from 20 to 30° C.

Depending on the $SiO_2$ source and/or Al source, it is possible, that one or more alcohols are formed in the mixture according to (i) by, for example, hydrolysis. According to a particularly preferred embodiment, this at least one alcohol is separated off before the crystallization of the zeolite material. It is possible to use all suitable separation methods, distilling off being particularly preferred. Here, the distillation can preferably be effected, for example, at atmospheric or reduced pressure. More preferably, the at least one alcohol is distilled off at bottom temperatures of from 85 to 95° C., in particular from 90 to 95° C.

Accordingly, the present invention also relates to a process as described above, wherein the alcohol which is formed in the mixture according to (i) is distilled off prior to the reaction according to (ii).

In the process according to the present invention, it is possible to add the at least one aluminum source to the reaction mixture before or after the at least one alcohol is separated off. According to a preferred embodiment, the addition of the at least one aluminum source is effected after the at least one alcohol has been separated off.

According to a more preferred embodiment of the process according to the present invention, the mixture obtained after separating off the at least one alcohol obtained from the hydrolysis, more preferably the bottom product obtained from the distillation, is mixed with, particularly preferably, water, more preferably with demineralized water. Preferably, the amount of water added is such that the distillation loss is roughly compensated.

The reaction according to (ii), from which crystalline zeolite material in its mother liquor is obtained, preferably takes place at a temperature in the range of from 150 to 180° C., particularly preferably in the range of from 160 to 180° C., in particular in the range of from 170 to 180° C.

According to a particularly preferred embodiment of the process according to the present invention, the reaction according to (ii) takes place in an autoclave, for example in a steel autoclave. More preferably, the reaction mixture is stirred at least during a part of the reaction time.

The duration of the reaction according to (ii) is preferably from 1 to 48, more preferably from 4 to 36, particularly preferably from 12 to 24, hours.

The pressure during this reaction according to (ii) is preferably from atmospheric pressure to 50 bar, more preferably in the range of from 5 to 25, particularly preferably in the range of from 10 to 15, bar.

Accordingly, the present invention also relates to a process as described above, wherein the reaction according to (ii) is carried out at a temperature in the range of from 150 to 180° C. in an autoclave with a reaction time of 1 to 48 hours.

According to a preferred embodiment, the pH of the mother liquor containing the crystalline zeolite material is brought into the range of from 5.5 to 7.5, preferably from 6 to 7, preferably after cooling to about room temperature and before the isolation according to (iii) by addition of at least one suitable compound.

Particularly preferably, suitable compounds here are Broenstedt acids, for example hydrochloric acid, sulfuric acid, phosphoric acid, nitric acid or carboxylic acids, dicarboxylic acids or oligo- or polycarboxylic acids, which can be used alone or as a mixture of two or more thereof. Furthermore, said acids can be used in concentrated form or in dilute solution. If the acids are used in solution, for example, water is particularly preferred as a solvent. Acids here are very particularly preferably those which can be removed in a subsequent calcination step, for example carboxylic acids or nitric acid.

According to a particularly preferred embodiment of the process according to the present invention, the crystalline zeolite material of the pentasil structure type, preferably of the structure type ZSM-5, is separated from its mother liquor by a suitable process according to (iii) and more preferably dried by one or more suitable methods and once again preferably subsequently calcined. The calcination can preferably be effected, for example, in a suitable gas atmosphere, wherein air and/or lean air are particularly preferably used as gas atmosphere.

All methods for separating the crystalline zeolite material from its mother liquor are conceivable. Inter alia, filtration methods, ultrafiltration methods, diafiltration methods or centrifuging methods or, for example, spray-drying methods or spray-granulation methods may be mentioned. The crystalline zeolite material is preferably separated from the mother liquor by ultrafiltration. According to a more preferred embodiment of the process according to the present invention the crystalline zeolite material is isolated from the mother liquor by filtration Accordingly, the present invention also describes a process as described above, wherein the zeolite material is isolated from the mother liquor by means of ultrafiltration according to (iii).

Accordingly, the present invention further also describes a process as described above, wherein the zeolite material is isolated from the mother liquor by means of filtration according to (iii), wherein in particular the adjustment of the pH value to a range of from 5.5 to 7.5 and preferably to a range of from 6 to 7, as described above, is carried out.

Prior to the isolation of the crystalline zeolite material from the mother liquor, it is possible to increase the content of zeolite material in the mother liquor by concentration. Details of the separation of the crystalline zeolite material from the mother liquor are also to be found in DE-A 10232 406.9, which is hereby fully incorporated into the present application by reference. For example the membrane used for ultrafiltration according to an embodiment according to the present invention can contain separation layers with pore diameters of from 10 to 500 nm, wherein the geometry of the at least one membrane for example is selected from the group consisting of flat-geometry, tube-geometry, multi-channel-element-geometry, capillary-geometry and winding-geometry. The transmembrane pressure occurring during the ultrafiltration is e.g. from 0.5 to 20 bar. The temperature at which the ultrafiltration is performed, is for example preferably in the range of from room temperature to 80° C., more preferably in the range of from 30 to 80° C.

The zeolite material separated from the mother liquor is preferably dried at temperatures in general in the range of from 80 to 160° C., preferably in the range of from 90 to 145° C., particularly preferably in the range of from 100 to 130° C., the duration of drying generally being 6 hours or more, for example in the range of from 6 to 24 hours. However, depending on the moisture content of the material to be dried, shorter drying times, for example about 1, 2, 3, 4 or 5 hours, are also possible.

The calcination subsequently carried out preferably at least once, wherein according to (iv), the at least one template compound and optionally the at least one acid described above are removed from the crystalline material, is carried out at temperatures in general in the range of from 400 to 750° C., preferably from 450 to 600° C., particularly preferably from 490 to 530° C.

The calcination can be effected under any suitable gas atmosphere, wherein air and/or lean air is preferred. Furthermore, the calcination is preferably carried out in a muffle furnace, rotary kiln and/or a belt calcination furnace, wherein the duration of calcination generally is 1 hour or more, for example in the range of from 1 to 24 or from 4 to 12 hours. Accordingly, it is possible in the process according to the present invention, for example, to calcine the zeolite material once, twice or more often for in each case at least 1 hour, for example in each case from 4 to 12, preferably from 4 to 8, hours, it being possible for the temperatures during a calcination step to remain constant or to be changed continuously or discontinuously. If calcination is effected twice or more often, the calcination temperatures in the individual steps may be different or identical.

Accordingly, the present invention also relates to a process as described above, wherein the crystalline material which is separated according to (iii) is first dried at a temperature in the range of from 80 to 160° C. and is subsequently calcined at a temperature in the range of from 400 to 750° C.

According to a further embodiment of the process according to the present invention, the zeolite can be subjected to at least one wash process after the separation and/or after the drying and/or after the calcination, wherein the crystalline material separated is brought into contact with at least one suitable wash substance. Very particularly preferably, the crystalline zeolite material is washed with water prior to drying. In the context of the present invention, the wash process can be effected either with water in the liquid state or with steam, wherein embodiments in which the wash process is carried out with both water in the liquid state and steam, simultaneously or in any desired sequence, are also possible. Preferably, washing is effected with liquid water.

If the treatment with steam is chosen, the separated zeolite material is particularly preferably exposed to steam at temperatures in the range of from 100 to 750° C., preferably from 100 to 250° C., particularly preferably from 120 to 175° C., this exposure preferably lasting for from 12 to 48 hours.

Very particularly preferably, this contacting takes place in an autoclave.

Accordingly the present invention also describes a process, as described above, wherein the zeolite material, after step (iv), is exposed to water in an autoclave.

In addition to or instead of the at least one wash process, the zeolite material separated can be treated with a concentrated or dilute Broenstedt acid or a mixture of two or more Broenstedt acids. Suitable acids are, for example, hydrochloric acid, sulfuric acid, phosphoric acid, nitric acid or carboxylic acids, dicarboxylic acids or oligo- or polycarboxylic acids, for example nitrilotriacetic acid, sulfosalicylic acid or ethylenediaminotetraacetic acid. According to a preferred embodiment of the process according to the present invention, the step, wherein the isolated zeolite material is treated with concentrated or diluted Broensted acid or a mixture of two ore more Broenstedt acids, is dispensed with.

Where the zeolite was dried and/or calcined after separation from the mother liquor as described above and was subjected to a wash process and/or treatment with at least one Broenstedt acid after the drying and/or the calcination, a further drying and/or calcination follows according to a particularly preferred embodiment of the present invention.

This drying is effected at temperatures in general in the range of from 80 to 160° C., preferably from 90 to 145° C., particularly preferably from 100 to 130° C. The calcination preferably effected subsequently is carried out at a temperature in general in the range of from 400 to 750° C., preferably from 450 to 600° C., particularly preferably from 490 to 530° C.

Accordingly the present invention also relates to a process, as described above, wherein the zeolitic material after step (iv) is exposed to water in an autoclave and is subsequently dried at a temperature in the range of from 80 to 160° C. and is subsequently calcined at a temperature in the range of from 400 to 750° C.

Likewise the present invention relates to a zeolite material of the pentasil type having an alkali metal and alkaline earth metal content of not more than 150 ppm and a molar Si to Al ratio in the range of from 250 to 1500, wherein at least 90% of the primary particles of the zeolite material are spherical and at least 95% by weight of the spherical primary particles of the zeolite material have a diameter of less than or equal to 1 μm and, which is obtainable by a process according to any one of the above described embodiments.

The zeolite material according to the present invention and/or the zeolite material prepared according to the invention in this manner can generally be used in all processes or operations in which the properties of a zeolite material are desired. Very particularly preferably, the zeolite material according to the present invention or zeolite material prepared according to the invention is used as catalyst in chemical reactions.

The present invention accordingly relates to the use of a zeolite material as described above, or of a zeolite material obtainable by a process as described above, as a catalyst.

Precisely in the area of catalysts, it is often desired by users to employ not the crystalline, catalytically active material per se but the material which is present in moldings. These moldings are required in many industrial processes in order, for example, to be able to operate chemical reactions expediently in, for example, tubular reactors or tube-bundle reactors by, inter alia, the fixed-bed procedure.

The present invention accordingly also relates to a molding containing a zeolite material as described above.

In general, the molding may comprise all conceivable compounds in addition to the zeolite material according to the present invention, provided that it is ensured that the resulting molding is suitable for the desired application.

In the context of the present invention, it is preferred to use at least one suitable binder material in the production of the molding. In this preferred embodiment, it is more preferred to prepare a mixture of zeolite material and the at least one binder material.

Accordingly, the present invention also describes a process for the production of a molding, containing a zeolite material as described above, comprising the step (I) preparation of a mixture containing a zeolite material as described above, or a zeolite material obtainable by a process as described above, and at least one binder material.

Suitable binder materials are in general all compounds which impart adhesion and/or cohesion between the particles of the zeolite material which are to be bound, which adhesion and cohesion are over and above the physisorption which may be present without a binder material. Examples of such binder materials are metal oxides, such as $SiO_2$, $Al_2O_3$, $TiO_2$, $ZrO_2$ or MgO or clays or mixtures of two or more of these compounds.

As $Al_2O_3$ binder materials, clay minerals and naturally occurring or synthetic aluminas, for example alpha-, beta-, gamma-, delta-, eta-, kappa-, chi- or theta-alumina and the inorganic or organometallic precursor compounds thereof, for example gibbsite, bayerite, boehmite, pseudoboehmite or trialkoxyaluminates, for example aluminum triisopropylate, are in particular suitable. Further preferred binder materials are amphiphilic compounds having a polar and a nonpolar moiety, and graphite. Further binder materials are, for example, clays, such as montmorillonites, kaolins, bentonites, halloysites, dickites, nacrites or anaxites.

These binder materials may be used as such. It is also possible in the context of the present invention to use compounds from which the binder is formed in at least one further step in the production of the moldings. Examples of such binder material precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate.

In the context of the present invention, binder materials which either completely or partly comprise $SiO_2$ or are a precursor of $SiO_2$ from which $SiO_2$ is formed in at least one further step in the production of the moldings are very particularly preferred. In this context, both colloidal silica and wet process silica and dry process silica can be used. These are very particularly preferably amorphous silica, wherein the size of the silica particles is in the range of from 5 to 100 nm and the surface area of the silica particles is in the range of from 50 to 500 $m^2/g$.

Colloidal silica, preferably as an alkaline and/or ammoniacal solution, more preferably as an ammoniacal solution, is commercially available, inter alia, as Ludox®, Syton®, Nalco® or Snowtex®.

Wet process silica is commercially available, inter alia, as Hi-Sil®, Ultrasil®, Vulcasil®, Santocel®, Valron-Estersil®, Tokusil® or Nipsil®.

Dry process silica is commercially available, inter alia, as Aerosil®, Reolosil®, Cab-O-Sil®, Fransil® or ArcSilica®.

Inter alia, an ammoniacal solution of colloidal silica is preferred in the context of the present invention.

Accordingly, the present invention also relates to a molding as described above, additionally containing $SiO_2$ as binder material.

The present invention also relates to a process as described above, wherein the binder material employed according to (I) is $SiO_2$-containing or -forming binder material.

Accordingly, the present invention also relates to a process as described above, wherein the binder material is a colloidal silica.

The binder materials are preferably used in an amount which leads to the finally resulting moldings, whose binder content is up to 80, more preferably from 5 to 80, more preferably from 10 to 70, more preferably from 10 to 60, more preferably from 15 to 50, more preferably from 15 to 45, particularly preferably from 15 to 40, % by weight, based in each case on the total weight of the finally resulting molding.

The mixture of binder material or precursor for a binder material and the zeolite material can be mixed with at least one further compound for further processing and for forming a plastic mass. Inter alia, pore formers are preferred here.

Pore formers which may be used in the process according to the present invention are all compounds which, with regard to the prepared molding, provide a certain pore size, a certain pore size distribution and/or a certain pore volume.

Preferably used pore formers in the process according to the present invention are polymers which are dispersible, suspendable or emulsifiable in water or in aqueous solvent mixtures. Preferred polymers here are polymeric vinyl compounds, for example polyalkylene oxides, such as polyethylene oxides, polystyrene, polyacrylates, polymethacrylates, polyolefins, polyamides and polyesters, carbohydrates, such as cellulose or cellulose derivatives, for example methylcellulose, or sugar or natural fibers. Further suitable pore formers are, for example, pulp or graphite.

If pore formers are used in the preparation of the mixture according to (i), the polymer content of the mixture according to (i) is preferably in the range of from 5 to 90, more preferably from 15 to 75, particularly preferably from 25 to 55, % by weight, based in each case on the amount of zeolite material in the mixture according to (i).

If it is desirable for the pore size distribution to be achieved, a mixture of two or more pore formers may also be used.

In a particularly preferred embodiment of the process according to the present invention, as described below, the pore formers are removed in a step (V) by calcination to give the porous molding. According to a preferred embodiment of the process according to the present invention, moldings which have pores in the range of at least 0.6, preferably from 0.6 to 0.8, particularly preferably from more than 0.6 to 0.8, ml/g, determined according to DIN 66134, are obtained.

The specific surface area of the molding according to the present invention, determined according to DIN 66131, is in general at least 350 $m^2/g$, preferably at least 400 $m^2/g$, particularly preferably at least 425 $m^2/g$. For example, the specific surface area may be from 350 to 500 $m^2/g$ or from 400 to 500 $m^2/g$ or from 425 to 500 $m^2/g$.

Accordingly, the present invention also relates to a molding as described above, having a specific surface area of at least 350 $m^2/g$, containing pores having a pore volume of at least 0.6 ml/g.

In the preparation of the mixture according to (I), at least one pasting agent is added in a likewise preferred embodiment of the process according to the present invention.

Pasting agents which may be used are all compounds suitable for this purpose. These are preferably organic, in particular hydrophilic, polymers, for example cellulose, cellulose derivatives, such as methylcellulose, starch, such as potato starch, wallpaper paste, polyacrylates, polymethacrylates, polyvinyl alcohol, polyvinylpyrrolidone, polyisobutene or polytetrahydrofuran.

In particular, compounds which also act as pore formers can accordingly be used as pasting agents.

In a particularly preferred embodiment of the process according to the present invention, as described below, these pasting agents are removed in a step (V) by calcination to give the porous molding.

According to a further embodiment of the present invention, at least one acidic additive is introduced during the preparation of the mixture according to (I). Organic acidic compounds can be removed by calcination in the preferred step (V), as described below, are very particularly preferred. Carboxylic acids, for example formic acid, oxalic acid and/or citric acid, are particularly preferred. It is also possible to use two or more of these acidic compounds.

The order of addition of the components of the mixture according to (I) which contains the zeolite material is not critical. It is possible both first to add the at least one binder material, subsequently the at least one pore former, the at least one acidic compound and finally the at least one pasting agent and it is possible to interchange the sequence with regard to the at least one binder material, the at least one pore former, the at least one acidic compound and the at least one pasting agent.

After the addition of the binder material to the zeolite-containing solid, to which optionally at least one of the compounds described above had already been added, the mixture according to (I) is as a rule homogenized for from 10 to 180 minutes. Inter alia, kneaders, edge mills or extruders are particularly preferably used for the homogenization. The mixture is preferably kneaded. On an industrial scale, treatment in an edge mill is preferred for homogenization.

Accordingly, the present invention also describes a process as described above, comprising the steps (I) preparation of a mixture containing a zeolite material as described above, or a zeolite material obtainable by a process as described above, and at least one binder material;

(II) kneading of the mixture.

In the homogenization, as a rule temperatures of from about 10° C. to the boiling point of the pasting agent and atmospheric or slightly superatmospheric pressure are employed. Subsequently at least one of the compounds described above can be optionally added. The mixture thus obtained is homogenized, preferably kneaded, until an extrudable plastic mass has formed.

The homogenized mixture is molded according to a more preferred embodiment of the present invention.

In the context of the present invention, preferred shaping methods are those in which the molding is effected by extrusion in conventional extruders, for example to give extrudates having a diameter of, preferably, from 1 to 10 mm, particularly preferably from 2 to 5 mm. Such extrusion apparatuses are described, for example, in Ullmann's Enzyklopädie der Technischen Chemie, 4th Edition, Vol. 2, page 295 et seq., 1972. In addition to the use of an extruder, a ram extruder may likewise preferably be used for the molding.

In principle, however, all known and/or suitable kneading and molding apparatuses and methods can be used for the shaping. Examples of these include:

(i) bricketting, i.e. mechanical pressing with or without addition of additional binder material;

(ii) pelleting, i.e. compacting by circular and/or rotational movements;

(iii) sintering, i.e. the material to be molded is subjected to a thermal treatment.

For example, the shaping can be selected from the following group, wherein the combination of at least two of these methods is explicitly included: bricketting by means of a ram press, roll press, ring-roll press, bricketting without binder; pelleting, melting, spinning techniques, deposition, foaming, spray-drying; combustion in a shaft furnace, convection furnace, travelling grate, rotary kiln, edge mill.

The compacting may take place at ambient pressure or at superatmospheric pressure, for example at from 1 to several hundred bar. Furthermore, the compacting may take place at ambient temperature or at a temperature higher than the ambient temperature, for example at from 20 to 300° C. If drying and/or combustion are part of the shaping step, temperatures of up to 1500° C. are conceivable. Finally, the compacting may take place in the ambient atmosphere or in a controlled atmosphere. Controlled atmospheres are, for example, inert gas atmospheres or reducing and/or oxidizing atmospheres.

Accordingly, the present invention also describes a process for the production of a molding as described above, comprising the steps (I) preparation of a mixture containing a zeolite material as described above, or a zeolite material obtainable by a process as described above, and at least one binder material;
(II) kneading of the mixture;
(III) molding of the kneaded mixture to give at least one molding.

The shape of the moldings produced according to the invention can be chosen as desired. In particular, inter alia spheres, oval shapes, cylinders or tablets are possible.

In the context of the present invention, the molding is particularly preferably carried out by extrusion of the kneaded mixture obtained according to (II), more preferably substantially cylindrical extrudates having a diameter in the range of from 1 to 20 mm, preferably from 1 to 10 mm, more preferably from 2 to 10 mm, and particularly preferably from 2 to 5 mm, being obtained as extrudates.

In the context of the present invention, step (III) is preferably followed by at least one drying step. This at least one drying step is effected at temperatures in general in the range of from 80 to 160° C., preferably from 90 to 145° C., particularly preferably from 100 to 130° C., wherein the duration of drying generally is 6 hours or more, for example in the range of from 6 to 24 hours. However, depending on the moisture content of the material to be dried, shorter drying times, for example about 1, 2, 3, 4 or 5 hours, are also possible.

Before and/or after the drying step, the preferably obtained extrudate can, for example, be milled Preferably, granules or chips having a particle diameter of from 0.1 to 5 mm, in particular from 0.5 to 2 mm, are obtained.

Accordingly, the present invention also describes a process for the production of a molding as described above, comprising the steps (I) preparation of a mixture containing a zeolite material as described above, or a zeolite material obtainable by a process as described above, and at least one binder material;
(II) kneading of the mixture;
(III) molding of the kneaded mixture to give at least one molding;
(IV) drying of the at least one molding.

In the context of the present invention, step (IV) is preferably followed by at least one calcination step. The calcination is carried out at a temperature in general in the range of from 350 to 750° C., preferably from 450 to 600° C.

The calcination can be effected under any suitable gas atmosphere, air and/or lean air being preferred. Furthermore, the calcination is preferably carried out in a muffle furnace, a rotary kiln and/or a belt calcination furnace, wherein the duration of calcination generally is 1 hour or more, for example in the range of from 1 to 24 or from 3 to 12 hours. Accordingly, it is possible in the process according to the present invention, for example, to calcine the moldings once, twice or more often for in each case at least one hour, for example in each case in the range of from 3 to 12 hours, wherein the temperatures during the calcination step can remain the same or can be changed continuously or discontinuously. If calcination is effected twice or more often, the calcination temperatures in the individual steps may be different or identical.

Accordingly, the present invention also relates to a process for the production of moldings as described above, comprising the steps (I) preparation of a mixture containing a zeolite material as described above, or a zeolite material obtainable by a process as described above, and at least one binder material;
(II) kneading of the mixture;
(III) molding of the kneaded mixture to give at least one molding;
(IV) drying of the at least one molding;
(V) calcination of the at least one dried molding.

After the calcination step, the calcined material can, for example, be comminuted. Preferably, granules or chips having a particle diameter of from 0.1 to 5 mm, in particular from 0.5 to 2 mm, are obtained.

Before and/or after the drying and/or before and/or after the calcination, the at least one molding can be treated with a concentrated or dilute Broenstedt acid or with a mixture of two or more Broenstedt acids. Suitable acids are, for example, hydrochloric acid, sulfuric acid, phosphoric acid, nitric acid or carboxylic acids, dicarboxylic acids or oligo- or polycarboxylic acids, such as nitrilotriacetic acid, sulfosalicylic acid or ethylenediaminotetraacetic acid.

Preferably, this at least one treatment with at least one Broenstedt acid is followed by at least one drying step and/or at least one calcination step, which in each case is carried out under the conditions described above.

According to a further preferred embodiment of the process according to the present invention, the catalyst extrudates can be subjected to a steam treatment for better hardening, after which once again preferably drying is effected at least once and/or calcination is effected at least once. For example, after at least one drying step and at least one subsequent calcination step, the calcined molding is subjected to steam treatment and then once again dried at least once and/or calcined at least once.

The moldings obtained according to the invention have hardnesses which are in general in the range of from 2 to 15 N, preferably in the range of from 5 to 15 N, particularly preferably from 10 to 15 N.

The present invention accordingly also relates to a molding as described above, having a cutting hardness of from 2 to 15 N.

In the present invention, the hardness described above was determined on an apparatus from Zwick, type BZ2.5/TS1S with a preliminary force of 0.5 N, a feed velocity under the preliminary force of 10 mm/min and a subsequent test velocity of 1.6 mm/min. The apparatus had a fixed turntable and a freely movable punch with built-in blade of 0.3 mm thickness. The movable punch with the blade was connected to a load cell for force pick-up and, during the measurement, moved toward the fixed turntable on which the catalyst molding to be investigated was present. The test apparatus was controlled by means of a computer which registered and evaluated the measured results. The value obtained is the mean value of the measurements for 10 catalyst moldings in each case. The catalyst moldings had a cylindrical geometry, wherein their average length corresponds to about twice to three times the diameter, and were loaded with the blade of 0.3 mm thickness with increasing force until the molding had been cut through. The blade was applied to the molding perpendicularly to the longitudinal axis of the molding. The force required for this purpose is the cutting hardness (unit N).

The present invention accordingly also relates to a molding, obtainable by a process according any one of the above mentioned embodiments.

The at least one molding according to the invention and/or the molding produced according to the invention can generally be used in all processes or operations in which the properties of the molding and in particular of the zeolite material according to the present invention contained in the molding or a zeolite material prepared according to the invention are desired. Very particularly preferably, the at least one molding according to the invention or the molding produced according to the invention is used as a catalyst in chemical reactions.

The present invention accordingly relates to the use of a molding as described above, or of a molding obtainable by a process as described above, as catalyst.

The zeolite material according to the present invention and/or the moldings according to the present invention are preferably used, for example, in the preparation of epsilon-caprolactam from cyclohexanone oxime and in the preparation of N-vinylpyrrolidone from N-hydroxyethylpyrrolidone.

The use of the zeolite material and/or of the molding in the selective synthesis of triethylenediamine (TEDA) is very particularly preferred.

The present invention accordingly also relates to the use as catalyst as described above, wherein the catalyst is employed for the selective synthesis of triethylenediamine.

TEDA (IUPAC name: 1,4-diazabicyclo[2.2.2]octane) is an important intermediate and final product in the chemical industry, which is used, mainly as such, as a catalyst in the preparation of polyurethanes. A large number of different syntheses, which differ mainly in the choice of the starting materials and of the catalysts used, exists for the preparation of TEDA.

For the preparation of TEDA, it is possible to use a range of different starting materials which contain a C2 building block and/or a nitrogen building block and which may be cyclic or acyclic. Examples of suitable starting materials comprise ethylenediamine, diethylenetriamine, ethanolamine, aminoethylethanolamine, piperazine, aminoethylpiperazine and hydroxyethylpiperazine. Frequently, a single starting material is used, but it is also advantageously possible to use mixtures of two or more suitable starting materials. Usually, water is also added to the reaction mixture. The composition of the product mixture is decisively influenced by the choice of the starting materials, wherein in particular the avoidance of the formation of byproducts, in addition to the availability of the starting materials, is an important aspect with regard to the specification in the working-up to be achieved. In most cases, for increasing the selectivity with respect to the desired product TEDA, the synthesis is carried out in such a way that only a partial conversion of the starting material or starting materials used occurs. The disadvantage of the low yield is accepted owing to the small amounts of undesired byproducts which can be achieved.

Very generally, the present invention therefore relates to a process for the selective preparation of triethylenediamine by reacting at least one starting material which has a structural unit (I)

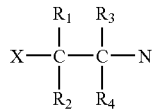

where $R_1$, $R_2$, $R_3$ and $R_4$, independently of one another, are an hydrogen atom or an alkyl group of 1 to 4 carbon atoms and X is an oxygen atom or nitrogen atom.

Examples of such compounds are, inter alia, ethylenediamine (EDA), monoethanolamine, diethanolamine, triethanolamine, piperazine (PIP), diethylenetriamine, triethylenetetramine, tri(2-aminoethyl)amine, N-(2-aminoethyl)ethanolamine, morpholine, N-(2-hydroxyethyl)piperazine, N,N'-bis(2-hydroxyethyl)piperazine, N-(2-aminoethyl)piperazine and N,N'-bis(2-aminoethyl)piperazine.

In the context of the present invention, it is, for example, preferably possible to prepare TEDA by using piperazine (PIP) as a starting material. It is also possible to use ethylenediamine (EDA) as a starting material. It is also possible to use a mixture of EDA and PIP as a starting material.

The present invention therefore relates to a process for the selective preparation of triethylenediamine by reacting a starting material consisting of
(A) x % by weight of piperazine and
(B) y % by weight of ethylenediamine,
where $x+y=100$ and $0 \leq x \leq 100$ and $0 \leq y \leq 100$, over a zeolite catalyst, wherein the zeolite catalyst contains a zeolite material as claimed in any of claims 1 to 4 or a zeolite material obtainable as claimed in any of claims 10 to 14.

The process according to the present invention can be carried out batchwise and is preferably carried out continuously.

The reaction according to the present invention can be carried out in the liquid phase and is preferably carried out in the gas phase.

The reaction is preferably carried out in the presence of at least one solvent or diluent.

Suitable solvents or diluents are, for example, acyclic or cyclic ethers of 2 to 12 carbon atoms, such as dimethyl ether, diethyl ether, di-n-propyl ether or isomers thereof, MTBE, THF, pyran, or lactones, such as gamma-butyrolactone, polyethers, such as monoglyme, diglyme, etc., aromatic or aliphatic hydrocarbons, such as benzene, toluene, xylene, pentane, cyclopentane, hexane and petroleum ether, or mixtures thereof, and in particular also N-methylpyrrolidone (NMP) or water or aqueous organic solvents or diluents of the above-mentioned type. Furthermore, ammonia is suitable as a solvent or diluent.

A particularly preferably used solvent or diluent, in particular solvent, is water.

Suitable diluents when carrying out the reaction in the gas phase are also inert gases, such as nitrogen (for example over and above the saturation of the reactor feed) or argon. The reaction is preferably carried out in the gas phase in the presence of ammonia.

The starting components or the reactor feed are or is advantageously pre-tempered.

Suitable reactors in which the process according to the present invention is carried out are stirred containers, in particular tubular reactors and tube-bundle reactors.

The zeolite catalyst, preferably in the form of a molding, is arranged in the reactor, preferably as a fixed bed.

The reaction in the liquid phase can be effected, for example, by the suspension, trickle-bed or liquid-phase procedure.

The preferred reaction in the gas phase can be effected in a fluidized catalyst bed or, preferably, a fixed catalyst bed.

Where piperazine alone is used as the starting material, preferred procedures are those in which the reaction temperature is in the range of from 300 to 450° C., particularly preferably in the range of from 330 to 400° C. The pressure under which the reaction takes place is in the range of from 0.01 to 50, preferably from 0.5 to 20, bar and particularly preferably in the region of atmospheric pressure, plus the pressure drop which results during passage over the catalyst bed.

More particularly preferably, piperazine is used as a mixture with water, wherein it is more preferable to use a starting material stream which contains at least 10, preferably from 10 to 60, in particular from 20 to 60, % by weight of water, based in each case on the total weight of the starting material stream containing piperazine and water.

Where piperazine is used as the only starting material, a WHSV (weight hourly space velocity), based on piperazine used in the reaction, in the range of from 0.01 to 5 h$^{-1}$, more preferably in the range of from 0.02 to 1 h$^{-1}$, particularly preferably in the range of from 0.05 to 0.8 h$^{-1}$, is preferred.

Where EDA alone is used as the starting material, preferred procedures are those in which the reaction temperature is in the range of from 300 to 400° C., particularly preferably in the range of from 320 to 350° C. The pressure under which the reaction takes place is in the range of from 0.01 to 50, preferably in the range of from 0.5 to 20, bar and particularly preferably in the range of atmospheric pressure, plus the pressure drop which results during passage over the catalyst bed.

More particularly preferably, EDA is used as a mixture with water, wherein it is more preferred to use a starting material stream which contains not more than 50, preferably not more than 30, in particular not more than 10, % by weight of water, based in each case on the total weight of the starting material stream containing EDA and water.

Where EDA is used as the only starting material, a WHSV (weight hourly space velocity), based on EDA used in the reaction, in the range of from 0.01 to 5 h$^{-1}$, more preferably in the range of from 0.02 to 1 h$^{-1}$, particularly preferably in the range of from 0.05 to 0.8 h$^{-1}$, is preferred.

Where a mixture of PIP and EDA is used as the starting material, the reaction is preferably carried out in such a way that, during continuous operation in the steady state, from 10 to 50% by weight of water and from 90 to 50% by weight of PIP and EDA (sum of amounts in % by weight of the two compounds PIP and EDA), more preferably from 30 to 50% by weight of water and from 70 to 50% by weight of PIP and EDA, particularly preferably from 40 to 50% by weight of water and from 60 to 50% by weight of PIP and EDA, are fed in, wherein it is optionally possible to reduce or increase the amount of PIP or of EDA in favor of or at the expense of EDA or of PIP.

In this case, the reaction is preferably carried out in such a way that, in continuous operation, the starting material stream contains EDA and PIP in a weight ratio in the range of from 1:1 to 10:1, more preferably in the range of from 2:1 to 6:1, particularly preferably in the range of from 3:1 to 5:1, calculated in each case as the weight of EDA to the weight of PIP.

In the embodiment as described above, according to which from 35 to 60, for example about 40, % by weight of EDA are added, the reaction in the steady state can be carried out in such a way that EDA is converted substantially completely to TEDA and PIP, wherein PIP preferably is removed by distillation from the product stream, together with any intermediates and/or byproducts additionally present, and, if necessary after removal of at least one of these intermediates and/or byproducts, about the same amount of EDA is added and the resulting mixture containing EDA and PIP is recycled to the reaction.

This procedure is preferably carried out in such a way that the consumption of PIP on balance tends to zero, and consequently substantially no additional PIP is added during continuous operation.

In this procedure, it has surprisingly been found that the amount of EDA discharged tends to zero. The separation of the reactor discharge is therefore particularly simple.

A particular advantage of the process is that intermediate fractions which contain both TEDA and PIP can be recycled to the reaction.

Where a mixture of EDA and PIP is used as the starting material, preferred procedures are those in which the reaction temperature is in the range of from 290 to 400° C., preferably in the range of from 310 to 370° C., particularly preferably in the range of from 310 to 350° C. The pressure under which the reaction takes place is in the range of from 0.1 to 10, preferably in the range of from 0.8 to 2, bar and particularly preferably in the range of atmospheric pressure, plus the pressure drop which results during passage over the catalyst bed.

Where a mixture of EDA and PIP is used as the starting material, a WHSV (weight hourly space velocity), based on the amines used in the reaction, is preferably in the range of from 0.05 to 6 h$^{-1}$, more preferably in the range of from 0.2 to 2 h$^{-1}$, particularly preferably in the range of from 0.3 to 1 h$^{-1}$.

The use of the catalyst according to the present invention, preferably in the form of moldings, is distinguished, inter alia, by the fact that a very high catalyst life is achieved. This is in general more than 1000 hours, preferably at least 1200 hours, more preferably at least 1400 hours, more preferably at least 1600 hours, more preferably at least 1800 hours, particularly preferably at least 2000 hours. With constant reaction parameters, no deterioration of the conversion in the reaction was observed during the abovementioned catalyst lives.

Accordingly, the present invention also describes a process as described above, wherein the catalyst has a life of at least 1200 h.

Very particularly preferably, the catalyst is used at least partly in the H form. If a part of the catalyst is not used in the H form, this part is very particularly preferably used in the NH$_4^+$ form. Particularly preferably, the entire catalyst is used in the H form.

Accordingly, the present invention also relates to a process as described above, wherein at least a portion of the catalyst is used in the H form.

In a further embodiment of the process according to the present invention, the catalyst, after use and independently of its form, for example after a decrease in the activity and/or the selectivity, is regenerated by a process in which the regeneration is effected by specific burning off of the deposits responsible for the deactivation. An inert gas atmosphere which contains exactly defined amounts of oxygen-donating substances is preferably used for this purpose. Such a regeneration process is described, inter alia, in WO 98/55228 and DE 197 23 949 A1, the respective contents of which are hereby fully incorporated into the present application by reference.

After the regeneration, the activity and/or the selectivity of the catalyst have increased compared with the state immediately before the regeneration.

The zeolite catalyst used according to the invention and to be regenerated is heated, either in the reaction apparatus (reactor) or in an external oven, in an atmosphere which contains from 0.1 to about 20 parts by volume of oxygen-donating substances, particularly preferably from 0.1 to 20 parts by volume of oxygen, to a temperature in the range of from 250 to 800° C., preferably from 400 to 550° C., in particular from 450 to 500° C. The heating is preferably carried out at a heating rate of from 0.1° C./min to 20° C./min, preferably from 0.3° C./min to 15° C./min, in particular from 0.5° C./min to 10° C./min.

During this heating phase, the catalyst is heated to a temperature at which the generally organic deposits present there begin to decompose, while at the same time the temperature is regulated via the oxygen content and therefore does not increase in such a way that damage to the catalyst structure occurs. The slow increase of the temperature or dwelling at low temperature by adjusting the corresponding oxygen content and the corresponding heating power is a substantial step for preventing local overheating of the catalyst in the case of high organic loads of the catalyst to be regenerated.

When the temperature of the exit gas stream at the reactor exit decreases in spite of increasing amounts of oxygen-donating substances in the gas stream, the burning-off of the organic deposits is completed. The duration of the treatment is generally in each case from 1 to 30, preferably from about 2 to about 20, in particular from about 3 to about 10, hours.

The subsequent cooling of the catalyst thus regenerated is preferably carried out in such a way that the cooling does not take place too rapidly, since otherwise the mechanical strength of the catalyst may be adversely affected.

It may be necessary to subject the catalyst, after the regeneration by calcination, as described above, has been performed, to washing with water and/or dilute acids, for example hydrochloric acid, in order to remove any inorganic load of the catalyst which may remain due to contamination of the starting materials (traces of alkali metals, etc.). Further drying and/or further calcination of the catalyst can then be carried out.

In a further embodiment of the process according to the present invention, prior to the heating according to the regeneration procedure, the at least partly deactivated catalyst is washed with a solvent in the reactor used for the reaction or in an external reactor, in order to remove desired product still adhering. The washing is carried out in such a way that the desired products adhering in each case to the catalyst can be removed therefrom, but temperature and pressure are not chosen to be so high that the generally organic deposits are likewise removed. Preferably, the catalyst is only rinsed with a suitable solvent. Consequently, all solvents in which the respective reaction product is readily soluble are suitable for this wash process. The amount of solvent used and the duration of the wash process are not critical. The wash process can be repeated several times and can be carried out at elevated temperatures. When $CO_2$ is used as the solvent, supercritical pressure is preferred, otherwise the wash process can be carried out under atmospheric, superatmospheric or supercritical pressure. After the end of the wash process, the catalyst is generally dried. Although the drying process is generally not critical, the drying temperature should not too greatly exceed the boiling point of the solvent used for the washing, in order to avoid abrupt evaporation of the solvent in the pores, in particular in the micropores, since this may lead to damage to the catalyst as well.

In a preferred embodiment of the preparation process, the continuous process according to the present invention for the synthesis of TEDA need not be interrupted for the regeneration of the catalyst according to the present invention, in order to increase the throughput of the process. This can be achieved by the use of at least two reactors connected in parallel, which can be operated alternately.

The catalyst regeneration can be carried out in such a way that at least one of the reactors connected in parallel is decoupled from the respective reaction stage and the catalyst contained in this reactor is regenerated, at least one reactor always being available for the reaction of the starting material or of the starting materials in each stage in the course of the continuous process.

For improving its purity, the TEDA obtained according to the invention can be recrystallized from suitable solvents, for example pentane or hexane. In general, however, this is not required since TEDA can be prepared by the process according to the present invention with purities of at least 95% by weight, preferably at least 96% by weight, particularly preferably at least 97% by weight.

In a particular embodiment, the claimed TEDA preparation process is combined with the subsequent TEDA process according to DE 199 33 850 A1.

According to this combination, TEDA is first prepared as described above. In the subsequent working-up of the TEDA (e.g. by distillation), which may be a multistep process, the TEDA is vaporized, preferably in the last working-up stage (in particular distillation or rectification stage), and the TEDA vapor which, for example, is obtained at the top or in a side take-off of the distillation column and preferably has a purity greater than 95% by weight, in particular greater than 97% by weight, is introduced into a liquid solvent. This introduction of the TEDA vapor directly into a liquid solvent is also referred to below as a TEDA quench.

The introduction of the TEDA vapor into the liquid solvent is effected in a quench apparatus, for example preferably in a falling-film condenser (thin-film, trickle-film or downflow condenser) or in a jet apparatus. The TEDA vapor can be passed cocurrently or countercurrently with the liquid solvent. The introduction of the TEDA vapor from the top into the quench apparatus is advantageous. Tangential feeding of the liquid solvent at the top of the falling-film condenser or feeding of the liquid solvent through one or more nozzles in order to achieve complete wetting of the inner wall of the quench apparatus is furthermore advantageous.

In general, the temperature in the TEDA quench is established by bringing the solvent used and/or the quench apparatus to the temperature of from 20 to 100° C., preferably 30 to 60° C. The absolute pressure in the TEDA quench is in general from 0.5 to 1.5 bar.

In general, the procedure is effected in such a way that, depending on the type of solvent, solutions having a TEDA content of from about 1 to 50% by weight, preferably from 20 to 40% by weight are first obtained in the TEDA quench.

By subsequent crystallization of the TEDA from the resulting solution, pure TEDA of high quality is obtained.

The liquid solvent is generally selected from the group consisting of cyclic and acyclic hydrocarbons, chlorinated aliphatic hydrocarbons, aromatic hydrocarbons, alcohols, ketones, aliphatic carboxylic esters, aliphatic nitriles and ethers.

For the preparation of a solution of pure TEDA according to the above process combination, which can be used, for example, as a catalyst solution in the preparation of polyurethane foam, an alcohol (e.g. ethylene glycol, 1,4-butanediol or, preferably, dipropylene glycol) is preferably used as the solvent for the TEDA quench. The color number of a resulting 33% strength by weight TEDA solution in dipropylene glycol is less than 150 APHA, in particular less than 100 APHA, very particularly less than 50 APHA.

The solutions thus obtained generally have a shelf-life of more than 6, preferably more than 12, particularly preferably more than 24, months with respect to the color number.

For the preparation of pure (crystalline) TEDA according to the above process combination, an aliphatic hydrocarbon, in particular a saturated aliphatic hydrocarbon of 5 to 8 carbon atoms (e.g. hexane, heptane or, preferably, pentane) is preferably used as the solvent for the TEDA quench. The crystallization of the pure TEDA from the TEDA solution prepared according to the invention can be effected by the methods known to a person skilled in the art. The TEDA crystals obtained by a subsequent multistage, or preferably one-stage, crystallization have high purity (purity of in general at least 99.5, in particular at least 99.8, % by weight, PIP content less than 0.1, in particular less than 0.05, % by weight, N-ethylpiperazine content less than 0.02, in particular less than 0.01, % by weight) and the color number of a 33% strength by weight solution in dipropylene glycol is less than 50 APHA, in particular less than 30 APHA.

All APHA numbers are determined according to DIN ISO 6271.

The following examples and figures illustrate the invention.

FIGURES

FIG. 1: shows the particle size distribution of the zeolite material produced according to example 1. The particle size distribution was determined according to DIN 13320 using laser diffraction on a "Mastersizer 2000" (Module Hydro 2000G) from Malvern Instruments Ltd. In doing so, as solution to be analyzed a solution containing 0.14% by weight of ZSM-5 cystalls in deionised water at ambient temperature was used. This solution was prepared by diluting a solution which was obtained according to example 1, wherein this solution was the result from the cystallization step before treatment with $HNO_3$. The solution diluted according to the above described procedure had a refraction index of 1.503. According to FIG. 1, the particles show an average size of 0.15 µm with a coefficient of variation of 21%. In diagram 1, the x-axis shows the particle size in [µm], the y-axis shows the corresponding percentage of particles in [%].

Figure 2:
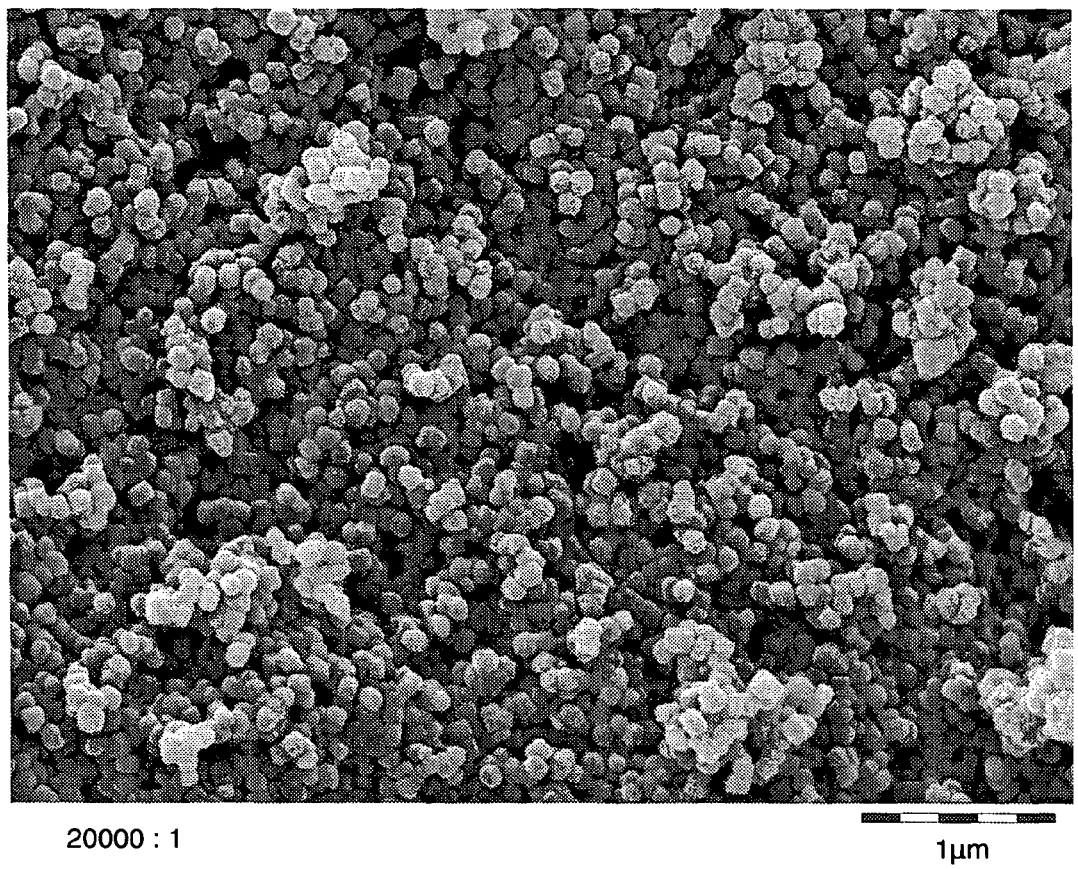

FIG. 2: shows a scanning electron micrograph (SEM) of the ZSM 5-powder, which was obtained according to example 1, using a resolution of 20000 to 1.

Figure 3:
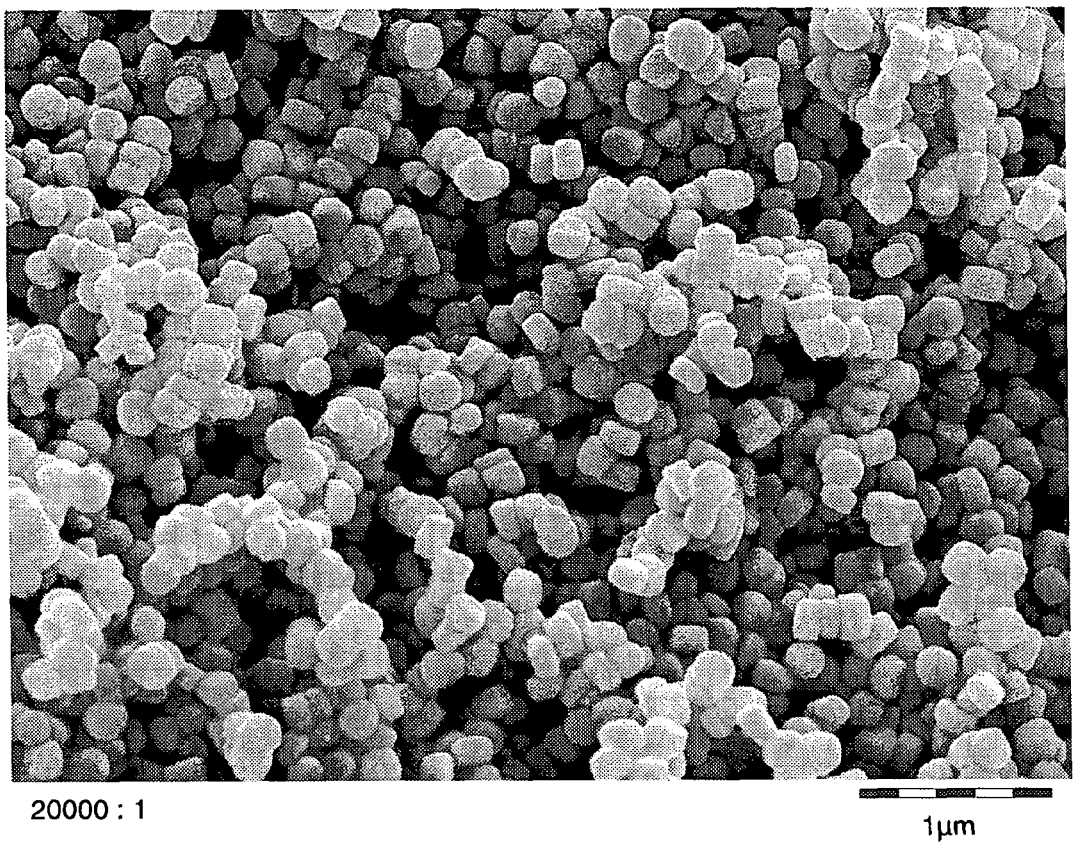

FIG. 3: shows a scanning electron micrograph (SEM) of the ZSM 5-powder, which was obtained according to example 4, using a resolution of 20000 to 1.

Figure 4:
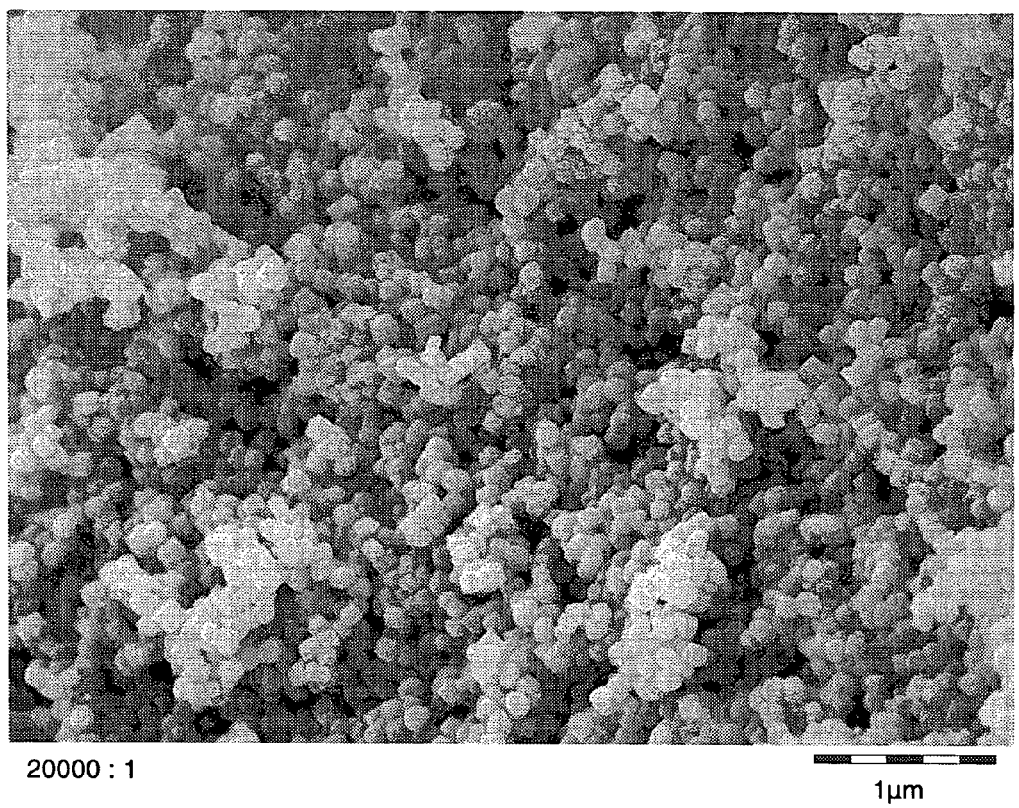

FIG. 4: shows a scanning electron micrograph (SEM) of the ZSM 5-powder, which was obtained according to example 7, using a resolution of 20000 to 1.

Figure 5:
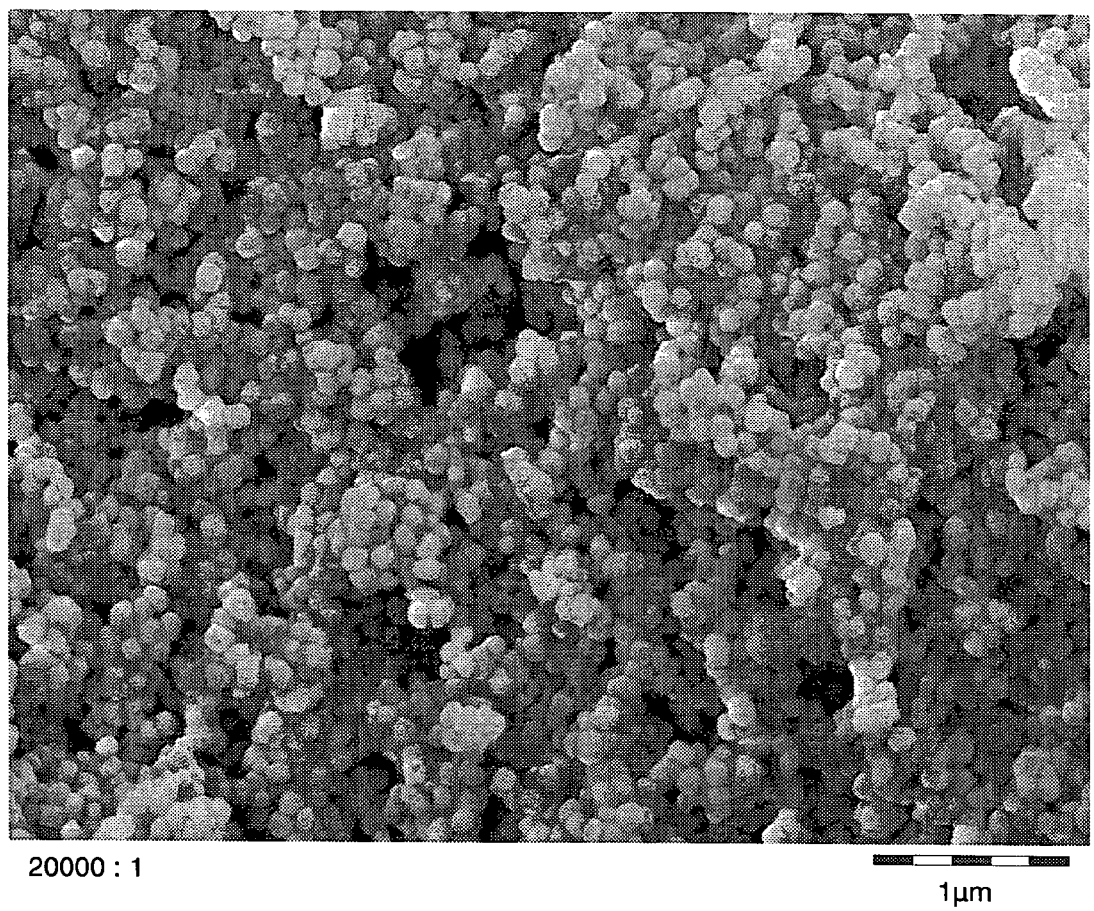

FIG. 5: shows a scanning electron micrograph (SEM) of the ZSM 5-powder, which was obtained according to example 10, using a resolution of 20000 to 1.

Figure 6:
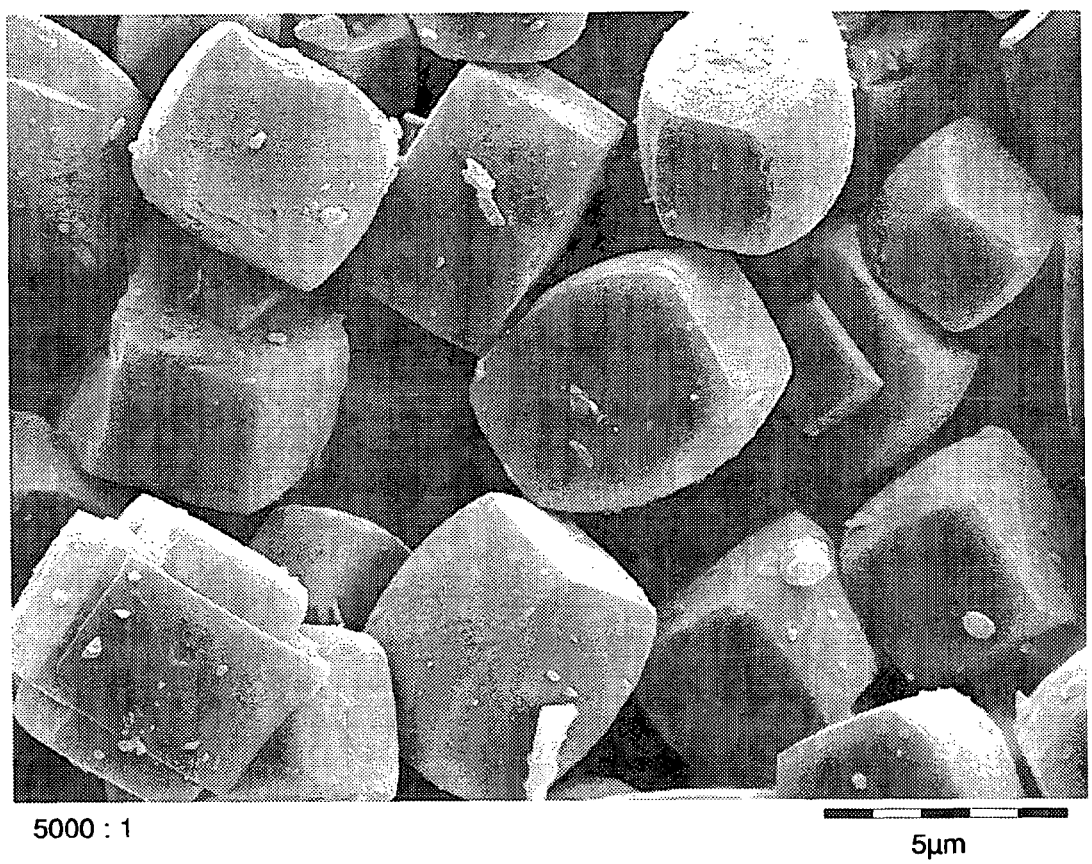

FIG. 6: shows a scanning electron micrograph (SEM) with a resolution of 5000 to 1 of the commercially available zeolite powder PZ-2/1000H (Fa. Zeochem, H-ZSM-5, molar Si:Al ratio of 500, rounded cuboid-like primary particles, with an edge length of a, b and c not longer than 5, 4 and 2 µm and an $Na_2O$ content of less than 100 mg/kg), which was used according to comparative example 4.

EXAMPLES

Example 1

Preparation of ZSM-5 Powder 920 g of TEOS (tetraethoxysilane) and 2.94 g of $Al_2(SO_4)_3 \cdot 18H_2O$ were initially taken in a four-necked flask, and 1620 g of a 20% strength TPAOH (tetra-propylammonium hydroxide) solution were introduced with stirring. The solution was stirred for 10 minutes at room temperature. The ethanol formed by hydrolysis was then distilled off under atmospheric pressure until a bottom temperature of 95° C. had been reached. 1485 g of synthesis gel were obtained.

742 g of the synthesis gel together with 742 g of demineralized water were filled into a 2.5 l steel autoclave, and the mixture was stirred for 24 hours at 175° C. under autogenous pressure. After cooling to room temperature, the suspension formed was titrated with concentrated $HNO_3$ to a pH of 7, and the suspension was filtered in a Büchner funnel and over a paper filter. The residue was washed twice with 500 ml of water each time, then dried in a drying oven at atmospheric pressure for 16 hours at 120° C. and then calcined in a muffle furnace with air metering for 5 hours at 500° C. 137 g of ZSM-5 powder were obtained. The electron micrograph of the ZSM-5 powder at $2\times10^4$ times magnification showed spherical primary particles having a diameter of in each case from 0.10 to 0.15 µm. The proportion of spherical primary particles was more than 97%. The $Na_2O$ content was less than 50 mg/kg. The molar Si:Al ratio was 460:1. The BET surface area, determined according to DIN 66131, was 461 $m^2/g$ and the pore volume, determined according to DIN 66134, was 1.10 $cm^3/g$.

Example 2

Production of a Molding Containing ZSM-5 Zeolite 134 g of ZSM-5 powder from example 1 were mechanically mixed together with 8.3 g of methylcellulose and 84 g of Ludox AS40 (from DuPont) in a kneader. Thereafter, 110 ml of demineralized water were added and the material was compacted for 60 minutes and then molded in a ram extruder at 45 bar pressure to give 2 mm extrudates. The extrudates were dried in a drying oven at atmospheric pressure for 16 hours at 120° C. and then calcined in a muffle furnace with air metering for 5 hours at 500° C. 138 g of ZSM-5 catalyst extrudates having a cutting hardness of 2.1 N were obtained. The BET surface area, determined according to DIN 66131, was 353 $m^3/g$ and the pore volume, determined according to DIN 66134, was 0.62 $cm^3/g$.

Example 3

Preparation of Triethylenediamine (TEDA) from Piperazine (PIP) and Ethylenediamine (EDA)

In a tubular reactor with secondary oil heating (length: 100 cm, internal diameter: 6 mm), filled with 20 ml (=11.4 g) of catalyst from example 2, a mixture of ethylenediamine (EDA), piperazine (PIP) and water in a weight ratio of 25/25/50 was subjected to a temperature of 350° C. and a space velocity, based on the two organic components EDA and PIP, of 0.50 g (organic components)/g (catalyst)/h. After an operating time of 75 hours, the reaction discharge was collected over a period of 1 hour and then investigated by gas chromatography. The analysis of the reaction discharge gave an EDA conversion of 97%, a PIP conversion of 48% and a TEDA selectivity of 95%.

Example 4

Preparation of ZSM-5 Powder

The preparation was carried out analogously to example 1, starting from 920 g of TEOS, 2.94 g of $Al_2(SO_4)_3 \cdot 18H_2O$ and 810 g of a 20% strength TPAOH solution. The yield was 133 g.

The electron micrograph at $2\times10^4$ times magnification showed spherical ZSM-5 primary particles. The proportion of spherical primary particles was more than 97%. The diameter of the spherical primary particles was from 0.20 to 0.25 µm.

For the spherical primary particles, which were cuboids having rounded edges, the maximum edge lengths a, b and c were 0.2, 0.2 and 0.15 µm. The $Na_2O$ content was less than 50 mg/kg. The molar Si:Al ratio was 470:1. The BET surface area, determined according to DIN 66131, was 440 $m^2/g$ and the pore volume, determined according to DIN 66134, was 0.98 $cm^3/g$.

Example 5

Production of a Molding Containing ZSM-5 Zeolite

The molding was carried out analogously to example 2, starting from 126 g of the ZSM-5 powder from example 4. 147 g of catalyst extrudates having a cutting hardness of 2.9 N were obtained. The BET surface area, determined according to DIN 66131, was 382 m$^2$/g and the pore volume, determined according to DIN 66134, was 0.64 cm$^3$/g.

Example 6

Preparation of Triethylenediamine (TEDA) from Piperazine (PIP) and Ethylenediamine (EDA)

The catalyst from example 5 was tested analogously to example 3. The analysis of the reaction discharge after an operating time of 43 hours gave an EDA conversion of 95%, a PIP conversion of 43% and a TEDA selectivity of 95%.

Example 7

Preparation of ZSM-5 Powder 460 g of TEOS were initially taken in a four-necked flask and 810 g of a 20% strength TPAOH solution were introduced with stirring. The solution was stirred for 10 minutes at room temperature. The ethanol formed by hydrolysis was then distilled off under atmospheric pressure until a bottom temperature of 95° C. had been reached. 698 g of synthesis gel without aluminum were obtained.

The synthesis gel was installed together with 698 ml of demineralized water and 1.84 g of Al$_2$(SO$_4$)$_3$.18H$_2$O in a 2.5 l steel autoclave. The reaction conditions and the working-up of the reaction mixture corresponded to those of example 1. 132 g of ZSM-5 powder were obtained.

The electron micrograph at 2×10$^4$ times magnification showed spherical ZSM-5 primary particles having a diameter of from 0.10 to 0.15 μm. The proportion of spherical primary particles was more than 97%. The Na$_2$O content was less than 50 mg/kg. The molar Si:Al ratio was 385:1. The BET surface area, determined according to DIN 66131, was 458 m$^2$/g and the pore volume, determined according to DIN 66134, was 1.24 cm$^3$/g.

Example 8

Production of a Molding Containing ZSM-5 Zeolite

The molding was carried out analogously to example 2, starting from 128 g of the ZSM-5 powder from example 7. 148 g of ZSM-5 catalyst extrudates having a cutting hardness of 3.2 N were obtained. The BET surface area, determined according to DIN 66131, was 364 m$^2$/g and the pore volume, determined according to DIN 66134, was 0.68 cm$^3$/g.

Example 9

Preparation of Triethylenediamine (TEDA) from Piperazine (PIP) and Ethylenediamine (EDA)

The catalyst from example 8 was tested analogously to example 3. The analysis of the reaction discharge after an operating time of 48 hours gave an EDA conversion of 98%, a PIP conversion of 46% and a TEDA selectivity of 94%.

Example 10

Treatment of ZSM-5 Powder 132 g of ZSM-5 powder from example 1 were stirred together with 1300 g of demineralized water in a 2.5 l steel autoclave for 24 hours at 175° C. and autogenous pressure. After cooling to room temperature, the suspension was filtered in a Büchner funnel and over a paper filter. The residue was washed once with 500 ml of water, then dried in a drying oven at atmospheric pressure for 16 hours at 120° C. and then calcined in a muffle furnace with air metering for 5 hours at 500° C. 121 g of treated ZSM-5 powder were obtained.

The electron micrograph at 2×10$^4$ times magnification showed spherical ZSM-5 primary particles having a diameter of from 0.10 to 0.15 μm. The Na$_2$O content was less than 150 mg/kg. The molar Si:Al ratio was 459:1. The BET surface area, determined according to DIN 66131, was 456 m$^2$/g and the pore volume, determined according to DIN 66134, was 1.12 cm$^3$/g.

Example 11

Production of a Molding Containing Treated ZSM-5 Zeolite

The molding was carried out analogously to example 2, starting from 121 g of the ZSM-5 powder from example 10. 137 g of ZSM-5 catalyst extrudates having a cutting hardness of 3.4 N were obtained. The BET surface area, determined according to DIN 66131, was 327 m$^2$/g and the pore volume, determined according to DIN 66134, was 0.69 cm$^3$/g.

Example 12

Preparation of Triethylenediamine (TEDA) from Piperazine (PIP) and Ethylenediamine (EDA)

The catalyst from example 11 was tested analogously to example 3. The analysis of the reaction discharge after an operating time of 47 hours gave an EDA conversion of 99%, a PIP conversion of 49% and a TEDA selectivity of 96%.

Example 13

Preparation of Triethylenediamine (TEDA) from Piperazine (PIP) and Ethylenediamine (EDA)

The experimental procedure was analogous to example 3 with the catalyst from example 11, starting from a mixture of ethylenediamine (EDA), piperazine (PIP) and water in a weight ratio of 40/10/50, at a temperature of 350° C. and a space velocity, based on the two organic components EDA and PIP, of 0.30 g (organic components)/g (catalyst)/h. The analyses of the reaction discharges after an operating time of 162, 716 and 1147 hours are summarized in table 1.

TABLE 1

| Operating time/h | EDA conversion/% | TEDA selectivity/% |
| --- | --- | --- |
| 162 | 98 | 93 |
| 716 | 97 | 93 |
| 1147 | 96 | 93 |

Accordingly, both the activity of the catalyst and the selectivity were improved by the water treatment of the ZSM-5 powder under hydrothermal conditions. Under PIP-neutral process conditions, an operating time of at least 1147 hours was achievable at constant TEDA selectivity and an EDA conversion of more than 95%.

Comparative Example 1

Preparation of ZSM-5 Powder with Addition of NaOH

The preparation of the ZSM-5 powder was carried out analogously to example 4 with additionally 0.80 g of NaOH. The yield was 135 g.

The electron micrograph at $2 \times 10^4$ times magnification showed spherical ZSM-5 primary particles having a diameter of from 0.10 to 0.15 μm. The $Na_2O$ content was 853 mg/kg. The molar Si:Al ratio was 475:1. The BET surface area, determined according to DIN 66131, was 464 $m^2$/g and the pore volume, determined according to DIN 66134, was 0.95 $cm^3$/g.

Comparative Example 2

Production of a Molding Containing Treated ZSM-5 Zeolite

The molding was carried out analogously to example 2, starting from 120 g of ZSM-5 powder from comparative example 1. 131 g of ZSM-5 catalyst extrudates having a cutting hardness of 6.1 N were obtained. The BET surface area, determined according to DIN 66131, was 332 $m^2$/g and the pore volume, determined according to DIN 66134, was 0.63 $cm^3$/g.

Comparative Example 3

Preparation of Triethylenediamine (TEDA) from Piperazine (PIP) and Ethylenediamine (EDA)

The catalyst from comparative example 2 was tested analogously to example 3. The analysis of the reaction discharge after an operating time of 30 hours gave an EDA conversion of 92%, a PIP conversion of 45% and a TEDA selectivity of 94%. The increased sodium concentration thus led to a reduction in the EDA conversion.

Comparative Example 4

Production of a Molding Containing Commercial ZSM-5 Zeolite 120 g of the commercially available zeolite powder PZ-2/1000H (from Zeochem, H-ZSM-5, molar Si:Al ratio of 500, rounded cuboid primary particles having maximum edge lengths a, b and c of 5, 4 and 2 μm and an $Na_2O$ content of less than 100 mg/kg) were molded analogously to example 2 with Ludox AS40. 133 g of ZSM-5 catalyst extrudates having a cutting hardness of 3.9 N were obtained. The BET surface area, determined according to DIN 66131, was 337 $m^2$/g and the pore volume, determined according to DIN 66134, was 0.23 $cm^3$/g.

Comparative Example 5

Preparation of Triethylenediamine (TEDA) from Piperazine (PIP) and Ethylenediamine (EDA)

The catalyst from comparative example 4 was tested analogously to example 3. The analysis of the reaction discharge after an operating time of 46 hours gave an EDA conversion of 98%, a PIP conversion of 42% and a TEDA selectivity of 88%.

The use of ZSM-5 having a particle size of more than 1 μm led to a significantly lower TEDA selectivity.

We claim:

1. A zeolite material of the pentasil type comprising an alkali metal and alkaline earth metal content of not more than 150 ppm and a molar ratio of Si to Al of from 250 to 1500, wherein at least 90% of the primary particles of the zeolite material are spherical and at least 95% by weight of the spherical primary particles have a diameter of less than or equal to 1 μm.

2. The zeolite material as claimed in claim 1, wherein a portion of the zeolite material has the structure type ZSM-5.

3. The zeolite material as claimed in claim 1, wherein the alkali metal and alkaline earth metal content of the zeolite material is not more than 100 ppm.

4. The zeolite material as claimed in claim 1, wherein the diameter of the spherical primary particles is from 50 to 250 nm.

5. The zeolite material as claimed in claim 1, wherein the molar ratio of Si to Al is in the range of from 250 to 750.

6. The zeolite material as claimed in claim 1, wherein the molar ratio of Si to Al is in the range of from 350 to 600.

7. A process for the preparation of a zeolite material, comprising the steps
   (i) providing a mixture containing at least one $SiO_2$ source, at least one aluminum source and at least one template compound, wherein the mixture contains not more than 150 ppm of alkali metal and alkaline earth metal and wherein the at least one $SiO_2$ source and the at least one aluminum source are used in a ratio which permits the formation of a crystalline material having a molar ratio of Si to Al of from 250 to 1500;
   (ii) reacting the mixture to give a mother liquor containing crystalline material, said crystalline material containing at least a portion of at least one template compound;
   (iii) separating the crystalline material from the mother liquor; and
   (iv) removing the at least one template compound from the crystalline material,
   the zeolite material comprising an alkali metal and alkaline earth metal content of not more than 150 ppm and a molar ratio of Si to Al of from 250 to 1500, wherein at least 90% of the primary particles of the zeolite material are spherical and at least 95% by weight of the spherical primary particles have a diameter of less than or equal to 1 μm.

8. The process as claimed in claim 7, wherein the $SiO_2$ source includes tetraalkoxysilane and the template compound includes at least one tetraalkylammonium hydroxide, and the mixture according to (i) additionally contains water.

9. The process as claimed in claim 8, wherein alcohol which is formed in the mixture according to (i) is distilled off prior to reacting the mixture according to (ii).

10. The process as claimed in claim 9, wherein the reacting the mixture according to (ii) is conducted at a temperature from 150 to 180° C. in an autoclave with a reaction time of 1 to 48 hours.

11. The process as claimed in claim 7, wherein the crystalline material separated according to (iii) is dried at a temperature from 100 to 160° C. and then calcined at a temperature from 450 to 700° C.

12. The process as claimed in claim 7, wherein, after step (iv), the zeolite material is exposed to water in an autoclave and is subsequently dried at a temperature from 80 to 160° C. and is subsequently calcined at a temperature from 400 to 750° C.

13. A zeolite material of the pentasil type obtainable by a process comprising the steps
(i) providing a mixture containing at least one $SiO_2$ source, at least one aluminum source and at least one template compound, wherein the mixture contains not more than 150 ppm of alkali metal and alkaline earth metal and wherein the at least one $SiO_2$ source and the at least one aluminum source are used in a ratio which permits the formation of a crystalline material having a molar ratio of Si to Al of from 250 to 1500;
(ii) reacting the mixture to give a mother liquor containing crystalline material, said crystalline material containing at least a portion of at least one template compound;
(iii) separating the crystalline material from the mother liquor; and
(iv) removing the at least one template compound from the crystalline material,
said zeolite material comprising an alkali metal and alkaline earth metal content of not more than 150 ppm and a molar ratio of Si to Al in a range of from 250 to 1500, wherein at least 90% of the primary particles of the zeolite material are spherical and at least 95% by weight of the spherical primary particles have a diameter in the range of from less than or equal to 1 μm.

* * * * *